United States Patent
Sun et al.

(10) Patent No.: US 7,214,535 B2
(45) Date of Patent: May 8, 2007

(54) GLYPHOSATE-TOLERANT 5-ENOLPYRUVYLSHIKIMATE-3-PHOSPHATE SYNTHASE AND THE GENE ENCODING THE SAME

(75) Inventors: Yicheng Sun, Beijing (CN); Yancheng Chen, Beijing (CN); Fengmei Li, Beijing (CN); Zhexian Tian, Beijing (CN); Min Lin, Beijing (CN); Yiping Wang, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 10/513,639

(22) PCT Filed: Aug. 5, 2002

(86) PCT No.: PCT/CN02/00539

§ 371 (c)(1),
(2), (4) Date: Jun. 10, 2005

(87) PCT Pub. No.: WO03/095649

PCT Pub. Date: Nov. 20, 2003

(65) Prior Publication Data

US 2006/0010511 A1    Jan. 12, 2006

(30) Foreign Application Priority Data

May 10, 2002 (CN) ............................ 02 1 17647
May 28, 2002 (CN) ............................ 02 1 17991

(51) Int. Cl.
*C12N 15/29* (2006.01)
*C12N 15/82* (2006.01)

(52) U.S. Cl. .................. 435/419; 435/320.1; 536/23.2; 800/300

(58) Field of Classification Search ............... 536/23.2, 536/23.7; 435/320.1, 419; 800/300, 278, 800/288

See application file for complete search history.

(56) References Cited

U.S. PATENT DOCUMENTS

| 4,971,908 A | 11/1990 | Kishore et al. ............ 536/23.2 |
| 5,310,667 A | 5/1994 | Eichholtz et al. .......... 435/91.1 |
| 5,627,061 A | 5/1997 | Barry et al. ................ 800/288 |
| 5,633,435 A * | 5/1997 | Barry et al. ................ 800/288 |
| 5,866,775 A | 2/1999 | Eichholtz et al. ........... 800/260 |
| 2002/0007053 A1 | 1/2002 | Barry et al. | |

OTHER PUBLICATIONS

Guo et al 2004, Proc. Natl. Acad. Sci. USA 101: 9205-9210.*
Hill et al 1998, Biochem. Biophys. Res. Comm. 244:573-577.*
Lazar et al 1988, Mol. Cell. Biol. 8:1247-1252.*
Sun et al 2005, Applied and Environmental Microbiology 71(8): 4771-4776.*

* cited by examiner

*Primary Examiner*—David H Kruse
(74) *Attorney, Agent, or Firm*—Fish & Richardson P.C.

(57) ABSTRACT

The present invention relates to a novel 5-enolpyruvylshikimate-3-phosphate synthase (EPSPS). It is highly tolerant to glyphosate, the competitive inhibitor of the substrate phosphoenolpyruvate (PEP). The invention also relates to a gene encoding the synthase, a construct and a vector comprising said gene, and a host cell transformed with said construct or vector.

23 Claims, 8 Drawing Sheets

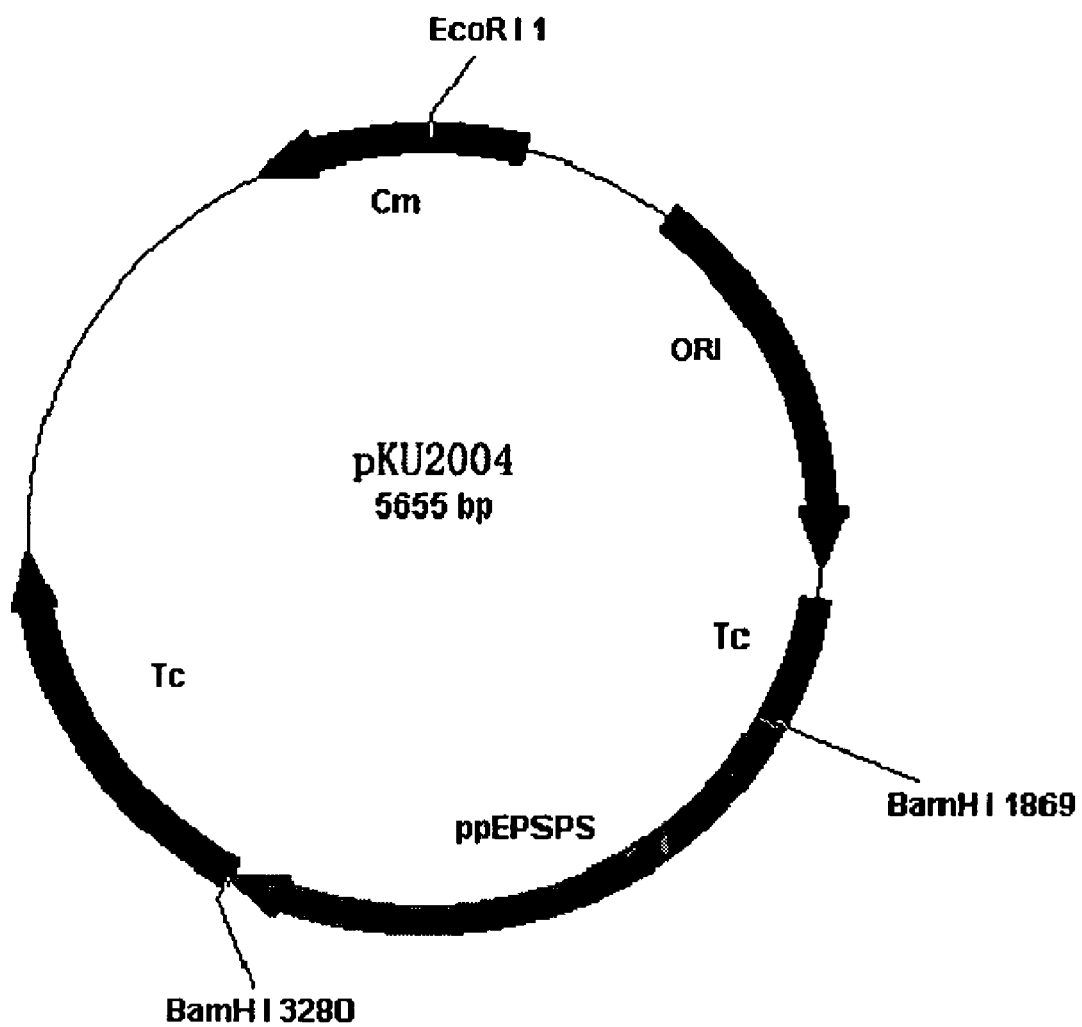
Fig. 1 The map of plasmid pKU2004

Fig.2 The amino acid sequence alignment between EPSPS of
*Pseudomonas putida P. P4G-1* with various known EPSPSs.

Origin

| | | |
|---|---|---|
| P. P4G-1 | ................................MQRACAA | 7 |
| C. ACETOBUTYLICUM | .......MNCVKINPCCLKGDIKIPPSKSLGHRAIICAAL | 33 |
| PG2982 | MSHSASPKPATARRSEALTGEIRIPGDKSISHRSFMFGGL | 40 |
| LBAA | MSHSASPKPATARRSEALTGEIRIPGDKSISHRSFMFGGL | 40 |
| AGROBACTERIUM CP4 | MSHGASSRPATARKSSGLSGTVRIPGDKSISHRSFMFGGL | 40 |
| B. SUBTILIS | .........MKRDKVQTLHGEIHIPGDKSISHRSVMFGAL | 31 |
| S. AUREUS | .....MVSEQIIDISGPLKGEIEVPGDKSMTHRAIMLASL | 35 |
| D. NODOSUS | ....MMTNIWHTAPVSALSGEITICGDKSMSHRALLLAAL | 36 |
| E. COLI | ......MESLTLQPIARVDGTINLPGSKSVSNRALLLAAL | 34 |
| A. SALMONICIDA | ......MNSLRLEPISRVAGEVNLPGSKSVSNGALLLAAL | 34 |
| A. THALIANA | .....KASEIVLQPIREISGLIKLPGSKSLSNRILLLAAL | 35 |
| N. TABACUM | .....KPNEIVLQPIKDISGTVKLPGSKSLSNRILLLAAL | 35 |
| P. HYBRIDA | .....KPSEIVLQPIKEISGTVKLPGSKSLSNRILLLAAL | 35 |
| Z. MAYS | ....AGAEEIVLQPIKEISGTVKLPGSKSLSNRILLLAAL | 36 |
| B. PERTUSSIS | ...MSGLAYLDLPAARLARGEVALPGSKSISNRVLLLAAL | 37 |
| | | |
| P. P4G-1 | ALVAKGISEIINPGHSNDDKAARDIVSRLGARLEDQPDGS | 47 |
| C. ACETOBUTYLICUM | SEEESTIENISYSKDIKATCIGMSKLGALIIEDAKDNSTL | 73 |
| PG2982 | ASGETRITGLLEGEDVINTGRAMQAMGAKIRKEGDVWIIN | 80 |
| LBAA | ASGETRITGLLEGEDVINTGRAMQAMGAKIRKEGDVWIIN | 80 |
| AGROBACTERIUM CP4 | ASGETRITGLLEGEDVINTGKAMQAMGARIRKEGDTWIID | 80 |
| B. SUBTILIS | AAGTTTVKNFLPGADCLSTIDCFRKMGVHIEQSSSDVVIH | 71 |
| S. AUREUS | AEGTSNIYKPLLGEDCRRTMDIFRLLGVDIKEDEDKLVVN | 75 |
| D. NODOSUS | AEGQTEIRGFLACADCLATRQALRALGVDIQREKEIVTIR | 76 |
| E. COLI | AHGKTVLTNLLDSDDVRHMLNALTALGVSYTLSADRTRCE | 74 |
| A. SALMONICIDA | ARGTTRLTNLLDSDDIRHMLAALTQLGVKYKLSADKTECT | 74 |
| A. THALIANA | SEGTTVVDNLLNSDDINYMLDALKRLGLNVETDSENNRAV | 75 |
| N. TABACUM | SKGRTVVDNLLSSDDIHYMLGALKTLGLHVEDDNENQRAI | 75 |
| P. HYBRIDA | SEGTTVVDNLLSSDDIHYMLGALKTLGLHVEEDSANQRAV | 75 |
| Z. MAYS | SEGTTVVDNLLNSEDVHYMLGALRTLGLSVEADKAAKRAV | 76 |
| B. PERTUSSIS | AEGSTEITGLLDSDDTRVMLAALRQLGVSVGEVADGCVTI | 77 |
| | | |
| P. P4G-1 | LQITSEGVKPVAPFIDCGESGLSIRMFTPIVALSKEEVTI | 87 |
| C. ACETOBUTYLICUM | KIKKQKLVSKEKVYIDCSESGSTVRFLIPISLIEERNVVF | 113 |

Fig.2(a) the amino acid sequence alignment between EPSPS of *Pseudomonas putida P. P4G-1* with various known EPSPSs.

| | | |
|---|---|---|
| PG2982 | GVGNGCLLQPEAALDFGNAGTGARLT............... | 106 |
| LBAA | GVGNGCLLQPEAALDFGNAGTGARLT............... | 106 |
| AGROBACTERIUM CP4 | GVGNGGLLAPEAPLDFGNAATGCRLT............... | 106 |
| B. SUBTILIS | GKGIDALKEPESLLDVGNSGTTIRLM............... | 97 |
| S. AUREUS | SPGYKAFKTPHQVLYTGNSGTTTRLL............... | 101 |
| D. NODOSUS | GVGFLGLQPPKAPLNMQNSGTSMRLL............... | 102 |
| E. COLI | IIGNGGPLHAEGALE....LFLGNAGTAMRPLAAALCLGS | 110 |
| A. SALMONICIDA | VHGLGRSFAVSAPVN....LFLGNAGTAMRPLCAALCLGS | 110 |
| A. THALIANA | VEGCGGIFPASIDSKSDIELYLGNAGTAMRPLTAAVTAAG | 115 |
| N. TABACUM | VEGCGGQFPVGKKSEEEIQLFLGNAGTAMRPLTAAVTVAG | 115 |
| P. HYBRIDA | VEGCGGLFPVGKESKEEIQLFLGNAGTAMRPLTAAVTVAG | 115 |
| Z. MAYS | VVGCGGKFPVEDA.KEEVQLFLGNAGTAMRPLTAAVTAAG | 115 |
| B. PERTUSSIS | EGVARFPTEQA...E....LFLGNAGTAFRPLTAALALMG | 110 |
| | | |
| P. P4G-1 | KGSGSLVTRPMDFFDEILPHLGVKVKSNQGK.LPLVIQGP | 126 |
| C. ACETOBUTYLICUM | DGQGKLSYRPLDSYFNIFDEKEIAYSHPEGKVLPLQIKGR | 153 |
| PG2982 | ............................MGLVGTYDMKT | 117 |
| LBAA | ............................MGLVGTYDMKT | 117 |
| AGROBACTERIUM CP4 | ............................MGLVGVYDFDS | 117 |
| B. SUBTILIS | ............................LGILAGRPFYS | 108 |
| S. AUREUS | ............................AGLLSGLGIES | 112 |
| D. NODOSUS | ............................AGILAAQRFES | 113 |
| E. COLI | NDIVLTGE..PRMKERPIGHLVDALRLGGAKITYLEQENY | 148 |
| A. SALMONICIDA | GEYMLGGE..PRMEERPIGHLVDCLALKGAHIQYLKKDGY | 148 |
| A. THALIANA | GNASYVLDGVPRMRERPIGDLVVGLKQLGADVECTLGTNC | 155 |
| N. TABACUM | GHSRYVLDGVPRMRERPIGDLVDGLKQLGAEVDCFLGTNC | 155 |
| P. HYBRIDA | GNSRYVLDGVPRMRERPISDLVDGLKQLGAEVDCFLGTKC | 155 |
| Z. MAYS | GNATYVLDGVPRMRERPIGDLVVGLKQLGADVDCFLGTDC | 155 |
| B. PERTUSSIS | GDYRLSGV..PRMHERPIGDLVDALRQFGAGIEYLGQAGY | 148 |
| | | |
| P. P4G-1 | LKPADVTVDGSLSSQFLTGLLLAYAAADASDVAIKVTNLK | 166 |
| C. ACETOBUTYLICUM | LKAGMFNLPGNISSQFISGLMFSLPFLEGDSIINITTNLE | 193 |
| PG2982 | SFIGDASLSKRPMGRVLNPLREMGVQVEAADGDRMPLTLI | 157 |
| LBAA | SFIGDASLSKRPMGRVLNPLREMGVQVEAADGDRMPLTLI | 157 |
| AGROBACTERIUM CP4 | TFIGDASLTKRPMGRVLNPLREMGVQVKSEDGDRLPVTLR | 157 |

Fig.2(b) the amino acid sequence alignment between EPSPS of *Pseudomonas putida P. P4G-1* with various known EPSPSs.

| | | |
|---|---|---|
| B. SUBTILIS | AVAGDESIAKRPMKRVTEPLKKMGAKIDGRAGGEFTPLSV | 148 |
| S. AUREUS | VLSGDVSIGKRPMDRVLRPLKLMDANIEGIEDNY.TPLII | 151 |
| D. NODOSUS | VLCGDESLEKRPMQRIITPLVQMGAKIVSHSNFTAPLHIS | 153 |
| E. COLI | PPLRLQGGFTGGNVD.VD.GSVSSQFLTALLMTAPLAPED | 186 |
| A. SALMONICIDA | PPLVVDAKGLWGGDVHVD.GSVSSQFLTAFLMAAPAMAPV | 187 |
| A. THALIANA | PPVRVNANGGLPGGKVKLSGSISSQYLTALLMSAPLALGD | 195 |
| N. TABACUM | PPVRIVSKGGLPGGKVKLSGSISSQYLTALLMAAPLALGD | 195 |
| P. HYBRIDA | PPVRIVSKGGLPGGKVKLSGSISSQYLTALLMAAPLALGD | 195 |
| Z. MAYS | PPVRVNGIGGLPGGKVKLSGSISSQYLSALLMAAPLALGD | 195 |
| B. PERTUSSIS | PPLRIGGGSIRVDGPVRVEGSVSSQFLTALLMAAPVLARR | 188 |
| | | |
| P. P4G-1 | SRPYIDLTLDVMKRFGLKTPENRNYEEFYFKAGNVYDETK | 206 |
| C. ACETOBUTYLICUM | SVGYVDMTIDMLKKFGIEIENKAYKSFFIKGNQKCKGTKY | 233 |
| PG2982 | GPKTANPITYRVPMASAQVKSAVLLAGLNTPGVTTVIEPV | 197 |
| LBAA | GPKTANPITYRVPMASAQVKSAVLLAGLNTPGVTTVIEPV | 197 |
| AGROBACTERIUM CP4 | GPKTPTPITYRVPMASAQVKSAVLLAGLNTPGITTVIEPI | 197 |
| B. SUBTILIS | SGASLKGIDYVSPVASAQIKSAVLLAGLQAEGTTTVTEPH | 188 |
| S. AUREUS | KPSVIKGINYQMEVASAQVKSAILFASLFSNDTTVIKELD | 191 |
| D. NODOSUS | GRPLT.GIDYALPLPSAQLKSCLILAGLLADGTTRLHTCG | 192 |
| E. COLI | TVIR.IKGDLV...SKPYIDITLNLMKTFGVEIENQHYQQ | 222 |
| A. SALMONICIDA | IPRIHIKGELV...SKPYIDITLHIMNSSGVVIEHDNYKL | 224 |
| A. THALIANA | VEIEIVDKLISVPYVEMTLKLMERFGVSVEHSDSWDRFFV | 235 |
| N. TABACUM | VEIEIIDKLISVPYVEMTLKLMERFGVSVEHTSSWDKFLV | 235 |
| P. HYBRIDA | VEIEIIDKLISVPYVEMTLKLMERFGISVEHSSSWDRFFV | 235 |
| Z. MAYS | VEIEIIDKLISIPYVEMTLRLMERFGVKAEHSDSWDRFYI | 235 |
| B. PERTUSSIS | SGQDITIEVVGELISKPYIEITLNLMARFGVSVRRDGWRA | 228 |
| | | |
| P. P4G-1 | MQRYTVEGDWSGGAFLLVAGAIAGPITVR.......... | 235 |
| C. ACETOBUTYLICUM | KVEGDFSQAAFWLSAGILNGNINCKDLNI.......... | 262 |
| PG2982 | MTRDHTEKMLQGFGADLTVETDKDGVRHIRITGQGKLVGQ | 237 |
| LBAA | MTRDHTEKMLQGFGADLTVETDKDGVRHIRITGQGKLVGQ | 237 |
| AGROBACTERIUM CP4 | MTRDHTEKMLQGFGANLTVETDADGVRTIRLEGRGKLTGQ | 237 |
| B. SUBTILIS | KSRDHTERMLSAFGVKLSEDQTSVSIAGGQ.....KLTAA | 223 |
| S. AUREUS | VSRNHTETMFRHFNIPIEAERLSITTTPDA.....IQHIK | 226 |
| D. NODOSUS | ISRDHTERMLPLFGGALEIKKEQIIVTGGQ.....KLHGC | 227 |

Fig.2 (c) the amino acid sequence alignment between EPSPS of *Pseudomonas putida* P. P4G-1 with various known EPSPSs.

| | | |
|---|---|---|
| E. COLI | FVVKGGQSYQSPGTYLVEGDASSASYFLAAAAIKGGTVKV | 262 |
| A. SALMONICIDA | FYIKGNQSIVSPGDFLVEGDASSASYFLAAGAIKGKVR.V | 263 |
| A. THALIANA | K...GGQKYKSPGNAYVEGDASSACYFLAGAAITGETVTV | 272 |
| N. TABACUM | R...GGQKYKSPGKAYVEGDASSASYFLAGAAVTGGTVTV | 272 |
| P. HYBRIDA | R...GGQKYKSPGKAFVEGDASSASYFLAGAAVTGGTITV | 272 |
| Z. MAYS | K...GGQKYKSPKNAYVEGDASSASYFLAGAAITGGTVTV | 272 |
| B. PERTUSSIS | FTIARDAVYRGPGRMAIEGDASTASYFLALGAIGGGPVRV | 268 |
| | | |
| P. P4G-1 | .....GLDIASTQADKAIVQALMSANAGIAIDAKEIKLHP | 270 |
| C. ACETOBUTYLICUM | .....SSLQGDKVILDILKKMGG......AIDEKSFSSKK | 291 |
| PG2982 | TIDVPGDPSSTAFPLVAALLVEGSDVTIRNVLMNPTRTGL | 277 |
| LBAA | TIDVPGDPSSTAFPLVAALLVEGSDVTIRNVLMNPTRTGL | 277 |
| AGROBACTERIUM CP4 | VIDVPGDPSSTAFPLVAALLVPGSDVTILNVLMNPTRTGL | 277 |
| B. SUBTILIS | DIF..VPGDISSAAFFLAAGAMVPNSRIVLKNVGLNPTRT | 261 |
| S. AUREUS | PADFHVPGDISSAAFFIVAALITPESDVTIHNVGINPTRS | 266 |
| D. NODOSUS | VLD..IVGDLSAAAFFMVAALIAPRAEVVIRNVGINPTRA | 265 |
| E. COLI | TGIGRNSMQGDIRFADVLEKMGATICWGDDYISCTRGELN | 302 |
| A. SALMONICIDA | TGIGKHSI.GDIHFADVLERMGARITWGDDFIEAEQGPLH | 302 |
| A. THALIANA | EGCGTTSLQGDVKFAEVLEKMGCKVSWTENSVTVTGPPRD | 312 |
| N. TABACUM | EGCGTSSLQGDVKFAEVLEKMGAEVTWTENSVTVKGPPRN | 312 |
| P. HYBRIDA | EGCGTNSLQGDVKFAEVLEKMGAEVTWTENSVTVKGPPRS | 312 |
| Z. MAYS | EGCGTTSLQGDVKFAEVLEMMGAKVTWTETSVTVTGPPRE | 312 |
| B. PERTUSSIS | TGVGEDSIQGDVAFAATLAAMGADVRYGPGWIETRGVRVA | 308 |
| | | |
| P. P4G-1 | ADLNAFEFDATDCPDLFPPLV....ALASYCKGETKIKGV | 306 |
| C. ACETOBUTYLICUM | SHTHGIVIDASQCPDLVPILS....VVAALSEGTTKIVNA | 327 |
| PG2982 | ILTLQEMGADIEVLNARLAGGEDVADLRVRASKLKGVVVP | 317 |
| LBAA | ILTLQEMGADIEVLNARLAGGEDVADLRVRASKLKGVVVP | 317 |
| AGROBACTERIUM CP4 | ILTLQEMGADIEVINPRLAGGEDVADLRVRSSTLKGVTVP | 317 |
| B. SUBTILIS | GIIDVLQNMGAKLEIKPSADSGAEPYGDLIIETSSLKAVE | 301 |
| S. AUREUS | GIIDIVEKMGGNIQLFNQTTGAEPTASIRIQYTPMLQPIT | 306 |
| D. NODOSUS | AIITLLQKMGGRIELHHQRFWGAEPVADIVVYHSKLRGIT | 305 |
| E. COLI | AIDMDMNH......IPDA..AMTIATAALFAKGTTTLRNI | 334 |
| A. SALMONICIDA | GVDMDMNH......IPDV...GHDHSGQSHCLPRVPPHSQH | 334 |
| A. THALIANA | AFGMRHLRAIDVNMNKMPDVAMTLAVVALFADGPTTIRDV | 352 |

Fig.2 (d) the amino acid sequence alignment between EPSPS of *Pseudomonas putida P. P4G-1* with various known EPSPSs.

| | | |
|---|---|---|
| N. TABACUM | SSGMKHLRAVDVNMNKMPDVAMTLAVVALFADGPTAIRDV | 352 |
| P. HYBRIDA | SSGRKHLRAIDVNMNKMPDVAMTLAVVALYADGPTAIRDV | 352 |
| Z. MAYS | PFGRKHLKAIDVNMNKMPDVAMTLAVVALFADGPTAIRDV | 352 |
| B. PERTUSSIS | EGGRLKAFDADFNLIPDA..AMTAATLALYADGPCRLRNI | 346 |
| | | |
| P. P4G-1 | SRL................................AHKES | 314 |
| C. ACETOBUTYLICUM | ARL................................RIKES | 335 |
| PG2982 | PERAPSMIDEYPVLAIAASFAEGETVMDGLDELRVKESDR | 357 |
| LBAA | PERAPSMIDEYPVLAIAASFAEGETVMDGLDELRVKESDR | 357 |
| AGROBACTERIUM CP4 | EDRAPSMIDEYPILAVAAAFAEGATVMNGLEELRVKESDR | 357 |
| B. SUBTILIS | IGGDIIPRLIDEIPIIALLATQAEGTTVIKDAAELKVKET | 341 |
| S. AUREUS | IEGELVPKAIDELPVIALLCTQAVGTSTIKDAEELKVKET | 346 |
| D. NODOSUS | VAPEWIANAIDELPIFFIAAACAEGTTFVGNLSELRVKES | 345 |
| E. COLI | YNW................................RVKET | 342 |
| A. SALMONICIDA | LQL................................AVRDD | 342 |
| A. THALIANA | ASW................................RVKET | 360 |
| N. TABACUM | ASW................................RVKET | 360 |
| P. HYBRIDA | ASW................................RVKET | 360 |
| Z. MAYS | ASW................................RVKET | 360 |
| B. PERTUSSIS | GSW................................RVKET | 354 |
| | | |
| P. P4G-1 | DRGLTLQDEFGKMGVEIHLEGDLMRVIGGKGVKGAEVSSR | 354 |
| C. ACETOBUTYLICUM | DRLKAMATELNKLGAEVVELEDGLLIEGKEKLKGGEVESW | 375 |
| PG2982 | LAAVARGLEANGVDCTEGEMSLTVRGRPDGKGLGGGT... | 394 |
| LBAA | LAAVARGLEANGVDCTEGEMSLTVRGRPDGKGLGGGT... | 394 |
| AGROBACTERIUM CP4 | LSAVANGLKLNGVDCDEGETSLVVRGRPDGKGLGNASGAA | 397 |
| B. SUBTILIS | NRIDTVVSELRKLGAEIEPTADGMKVYGKQTLKG...GAA | 378 |
| S. AUREUS | NRIDTTADMLNLLGFELQPTNDGLIIHPSEFKTN...ATV | 383 |
| D. NODOSUS | DRLAAMAQNLQTLGVACDVGADFIHIYGRSDRQF...LPA | 382 |
| E. COLI | DRLFAMATELRKVGAEVEEGHDYIRITPPEKLNFAEIATY | 382 |
| A. SALMONICIDA | RCTPCTHGHRRAQAGVSEEGTTFITRDAADPAQARRDRHL | 382 |
| A. THALIANA | ERMIAICTELRKLGATVEEGSDYCVITPPKKVKTAEIDTY | 400 |
| N. TABACUM | ERMIAICTELRKLGATVVEGSDYCIITPPEKLNVTEIDTY | 400 |
| P. HYBRIDA | ERMIAICTELRKLGATVEEGPDYCIITPPEKLNVTDIDTY | 400 |
| Z. MAYS | ERMVAIRTELTKLGASVEEGPDYCIITPPEKLNVTAIDTY | 400 |
| B. PERTUSSIS | DRIHAMHTELEKLGAGVQSGADWLEVAPPEPGGWRDAHIG | 394 |

Fig.2 (e) The amino acid sequence alignment between EPSPS of *Pseudomonas putida* P. P4G-1 with various known EPSPSs.

| | | |
|---|---|---|
| P. P4G-1 | HDHRIAMACAVAALKAVGETTIEHAEAVNKSYPDFYSDLK | 394 |
| C. ACETOBUTYLICUM | NDHRIAMALGIAALRCEESVTINGSECVSKSYPQFWSDLK | 415 |
| PG2982 | VATHLDHRIAMSFLVMGLAAEKPVTVDDSNMIATSFPEFM | 434 |
| LBAA | VATHLDHRIAMSFLVMGLAAEKPVTVDDSNMIATSFPEFM | 434 |
| AGROBACTERIUM CP4 | VATHLDHRIAMSFLVMGLVSENPVTVDDATMIATSFPEFM | 437 |
| B. SUBTILIS | VSSH.GDHRIGMMLGIASCITEEPIEIEHTDAIHVSYPTF | 417 |
| S. AUREUS | DSLT..DHRIGMMLAVASLLSSEPVKIKQFDAVNVSFPGF | 421 |
| D. NODOSUS | RVNSFGDHRIAMSLAVAGVRAAGELLIDDGAVAAVSMPQF | 422 |
| E. COLI | N..DHRMAMCFSLVALSDTPVTILDPKCTAKTFPDYFEQL | 420 |
| A. SALMONICIDA | Q..ASRIAMCFSLVALSDIAVTINDPGCTSKTFPDYFDKL | 420 |
| A. THALIANA | DDHRMAMAFSLAACADVPITINDSGCTRKTFPDYFQVLER | 440 |
| N. TABACUM | DDHRMAMAFSLAACADVPVTIKDPGCTRKTFPNYFDVLQQ | 440 |
| P. HYBRIDA | DDHRMAMAFSLAACADVPVTINDPGCTRKTFPNYFDVLQQ | 440 |
| Z. MAYS | DDHRMAMAFSLAACAEVPVTIRDPGCTRKTFPDYFDVLST | 440 |
| B. PERTUSSIS | TWDDHRMAMCFLLAAFGPAAVRILDPGCVSKTFPDYFDVY | 434 |
| | | |
| P. P4G-1 | QLGGVVSLNHQFNFS | 409 |
| C. ACETOBUTYLICUM | QLGGDVHEWSLGE | 428 |
| PG2982 | DMMPGLGAKIELSIL | 449 |
| LBAA | DMMPGLGAKIELSIL | 449 |
| AGROBACTERIUM CP4 | DLMAGLGAKIELSDTKAA | 455 |
| B. SUBTILIS | FEHLNKLSKKS | 428 |
| S. AUREUS | LPKLKLLENEG | 432 |
| D. NODOSUS | RDFAAAIGMNVGEKDAKNCHD | 443 |
| E. COLI | ARISQAA | 427 |
| A. SALMONICIDA | ASVSQAV | 427 |
| A. THALIANA | ITKH | 444 |
| N. TABACUM | YSKH | 444 |
| P. HYBRIDA | YSKH | 444 |
| Z. MAYS | FVKN | 444 |
| B. PERTUSSIS | AGLLAARD | 442 |

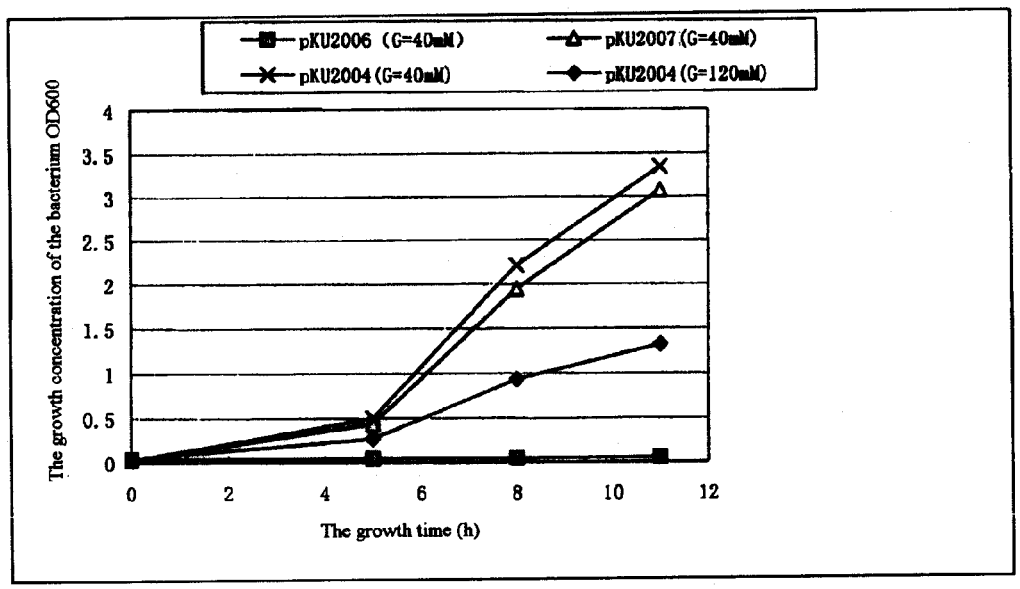
Fig.3 The growth curve of *E.coli* XL1-BLUE MR in different glyphosate concentrations, wherein said *E.coli* XL1-BLUE MR carries different EPSPS genes.

US 7,214,535 B2

GLYPHOSATE-TOLERANT 5-ENOLPYRUVYLSHIKIMATE-3-PHOSPHATE SYNTHASE AND THE GENE ENCODING THE SAME

TECHNICAL FIELD

The present invention relates to a novel glyphosate-tolerant 5-enolpyruvylshikimate-3-phosphate synthase (EPSPS), and isolated nucleic acid sequence encoding the synthase, a nucleic acid construct comprising said sequence or the coding region, a vector carrying said sequence or the coding region or said nucleic acid construct, and a host cell transformed with said construct or vector.

BACKGROUND

The 5-enolpyruvylshikimate-3-phosphate synthase (EPSPS) is a key enzyme involved in the aromatic amino acid synthesis pathway in plants and bacteria. Glyphosate, which is also referred to as N-phosphylmethyl glycine, is a broad-spectrum, highly efficient post-sprouting herbicide. Glyphosate is a competitive inhibitor of phosphoenolpyruvate (PEP), which is one of the substrates of EPSPS. Glyphosate block the conversion of PEP and 3-phosphate-shikimate to 5-enolpyruvul 3-phosphate-shikimate catalyzed by EPSPS, thereby block the synthesis pathway of shikimic acid, a precursor for the synthesis of aromatic amino acids, and lead to the death of plants and bacteria.

The glyphosate tolerance of a plant may be obtained by stably introducing a gene encoding glyphosate-tolerant EPSPS to the plant genome. There are mainly two classes of known glyphosate-tolerant EPSPS genes: Class I (see, e.g. U.S. Pat. No. 4,971,908; U.S. Pat. No. 5,310,667; U.S. Pat. No. 5,866,775) and Class II (see, e.g. U.S. Pat. No. 5,627,061; U.S. Pat. No. 5,633,435). These genes have been successfully introduced into plant genomes, and the glyphosate-tolerant plant cells and plants are obtained.

The invention is aimed to find a novel EPSPS of native sequence that is tolerant to glyphosate.

SUMMARY

An object of the invention is to provide a newly isolated nucleic acid sequence encoding glyphosate tolerant EPSPS protein.

A further object of the invention is to provide a novel glyphosate-tolerant EPSPS protein.

A further object of the invention is to provide a nucleic acid construct, formed by operably linking the above-said nucleic acid sequence to a control sequence essential for expressing said nucleic acid sequence in a selected host cell. Specifically, the control sequence includes optionally a promoter, an enhancer, a leader sequence, a polyadenylation signal, and the initiation and termination sequences for transcription and translation.

A further object of the invention is to provide a vector comprising the above-said nucleic acid sequence or nucleic acid construct.

A further object of the invention is to provide a host cell transformed with the above-said construct or vector. Said host cell may express the protein encoded by the above-said nucleic acid sequence under an appropriate condition, and enables said protein to exhibit enzymatic EPSPS activity and glyphosate tolerance, thereby the host cell obtains the glyphosate tolerance.

A further object of the invention is to provide the above-said host cell and progeny cells hereof. Said cells contain the aforesaid nucleic acid sequence or the coding region, or the nucleic acid construct or vector, and are glyphosate-tolerant.

The other purposes of the invention are illustrated in the following description and examples.

DISCLOSURE OF THE INVENTION

The invention provides a novel glyphosate-tolerant 5-enolpyruvylshikimate-3-phosphate synthase (EPSPS) having a native sequence. The term "native synthase" denotes a sequence which is not modified by mutagenesis, or by biological or chemical modifications, such as genetic engineering. The invention provides an isolated amino acid sequence of said EPSPS (SEQ ID NO:3). Any amino acid sequence which is modified by deletion, addition and/or substitution of one or more amino acid residues in SEQ ID NO:3 is included in the scope of the invention, provided that the modified sequence encodes a protein of EPSPS activity and glyphosate tolerance.

The invention further provides an isolated nucleic acid sequence encoding said EPSPS (SEQ ID NO:2, in particular the coding region). Any nucleic acid sequence which is modified by deletion, addition and/or substitution of one or more nucleotides in SEQ ID NO: 2 is included in the scope of the invention, provided that the modified sequence encodes a protein of EPSPS activity and glyphosate tolerance.

The nucleic acid construct of the invention is constructed by operably linking the EPSPS-encoding nucleic acid sequence of the invention with other homologous or heterologous sequence.

According to the method of the invention, the nucleic acid construct or the isolated nucleic acid sequence of the invention is incorporated into a vector, and a selected host cell is transformed with said vector. The EPSPS enzyme of the invention is expressed. The recombinant host cell is thus conferred with a tolerance to glyphosate. Alternatively, instead of transformation with a vector, the isolated nucleic acid sequence or the nucleic acid construct of the invention is introduced into a host cell directly by conventional methods such as electroporation. The EPSPS enzyme of the invention is expressed and the host cell is conferred with glyphosate tolerance. The vector and the recombinant host cell thus obtained, as well as the method for obtaining the cell are included in the scope of the invention.

DEFINITIONS

The term "percent (%) sequence homology" used herein refers to the percentage of amino acid residues in a candidate sequence that are identical with the amino acid residues in the target sequence, after aligning the sequences and introducing gaps, if necessary, to achieve the maximum percent sequence homology, and not considering any conservative substitutions as parts of the sequence homology. The sequences herein include amino acid sequences and nucleotide sequences. The determination of percent (%) sequence homology may be achieved in various ways that are within the skill in the art, for example, using publicly available computer software such as BLAST, BLAST-2, ALIGN, ALIGN-2 or Megalign (DNASTAR). Those skilled in the art can determine appropriate parameters for measuring alignment, including any algorithm needed to achieve maximal alignment over the full-length of the sequences being compared.

The term "nucleic acid construct" used herein refers to a single-stranded or double-stranded nucleic acid molecule, which is isolated from a native gene, or is modified to combine nucleic acid fragments in a manner not existing in nature. When the nucleic acid construct contains all the control sequences required for expressing the EPSPS of the invention, the term "nucleic acid construct" is synonymous to the term "expression cassette".

The term "control sequence" used herein comprises all components, which are essential or advantageous for the expression of a polypeptide of the present invention. Each control sequence may be native or foreign to the nucleic acid sequence encoding said polypeptide. Such control sequences include, but are not limited to, a leader sequence, polyadenylation sequence, a propeptide sequence, promoter, and transcription terminator. The control sequences include at least a promoter and termination signals for both transcription and translation. A control sequence may be provided with a linker to introduce specific restriction sites facilitating the ligation of the control sequence with the coding region of the nucleic acid sequence encoding a heterologous polypeptide.

The term "operably linking" denotes the linkage of the isolate nucleic acid sequence of the invention to any other sequences homologous or heterologous to said sequence, so that they together encode a product. When necessary, said sequences may be separated by methods such as restriction digest. The homologous or heterologous sequence as disclosed herein could be any sequence, such as any control sequence, that directs the expression of the isolated nucleic acid sequence of the invention in a selected host cell, or the sequence coding for a fusion protein together with the isolated nucleic acid sequence of the invention.

The term "host cell" used herein refers to any cell capable of receiving the isolated nucleic acid sequence of the invention, or receiving the construct or vector comprising said sequence, and keeping them stable therein. The host cell will obtain the feature determined by the isolated nucleic acid sequence of the invention when the cell contains said sequence.

DETAILED DESCRIPTION

The inventors surprisingly discover and isolate a novel glyphosate tolerant EPSPS coding gene. The coding sequence of said gene (SEQ ID NO:2) and the coding region (CDS, the nucleotides 574–1803) are disclosed herein. The amino acid sequence (SEQ ID NO:3) encoded by said CDS is also disclosed herein. DNAMAN version 4.0 is used with a CLUSTAL format to align the amino acid sequence as shown in SEQ ID NO:3 with the known sequences of EPSPS Classes I and II. It is found that the sequence of the invention does not comprise any sequence claimed by preceding patents (see FIG. 2). BLAST search in GenBank protein sequence bank shows that the SEQ ID NO:3 of the invention is 37% homologous with the EPSPS amino acid sequence derived from *Clostridium acetobutylicum*, and is 20% homologous with the EPSPS amino acid sequence derived from *E.coli* (see FIG. 2). NCBI-BLAST search indicates that the sequence as shown in nucleotides 574–1803 of SEQ ID NO:2 is not found to be homologous with any known nucleic acid sequence. Therefore, the nucleic acid sequence and the protein described in the invention are novel.

Hence, one aspect of the invention relates to an isolated nucleic acid sequence, which comprises the nucleic acid sequence shown in SEQ ID NO:2 and encodes a glyphosate tolerant EPSPS.

The invention also relates to an isolated nucleic acid sequence as shown in nucleotides 574–1803 of SEQ ID NO:2, which encodes a glyphosate tolerant EPSPS.

The invention also relates to a nucleic acid sequence obtained by modifying one or more nucleotides or by deleted and/or added 3 or a multiple of 3 nucleotides in SEQ ID NO:2 or in the sequence of nucleotides 574–1803 of SEQ ID NO:2, and said nucleotide sequence is capable of coding a protein with the activity of 5-enolpyruvylshikimate-3-phosphate synthase (EPSPS) and the glyphosate tolerance. The modification, deletion and addition of nucleotides are conventional within the skills in the art.

The invention also relates to a nucleotide sequence which is of the homology, such as the homology of at least about 65%, preferably at least about 66%, preferably at least about 67%, preferably at least about 68%, preferably at least about 69%, preferably at least about 70%, preferably at least about 71%, preferably at least about 72%, preferably at least about 73%, preferably at least about 74%, preferably at least about 75%, preferably at least about 76%, preferably at least about 77%, preferably at least about 78%, preferably at least about 79%, more preferably at least about 80%, more preferably at least about 81%, more preferably at least about 82%, more preferably at least about 83%, more preferably at least about 84%, more preferably at least about 85%, more preferably at least about 86%, more preferably at least about 87%, more preferably at least about 88%, more preferably at least about 89%, more preferably at least about 90%, more preferably at least about 91%, more preferably at least about 92%, more preferably at least about 93%, more preferably at least about 94%, more preferably at least about 95%, more preferably at least about 96%, more preferably at least about 97%, more preferably at least about 98%, most preferably at least about 99%, with the nucleic acid sequence defined by SEQ ID NO:2 or nucleotides 574–1803 of SEQ ID NO:2. Such a sequence is within the scope of the invention provided that it encodes a protein having the glyphosate tolerant EPSPS activity.

The isolated nucleic acid sequence of the invention may be cloned from nature with methods disclosed in Examples of the invention. The cloning method may comprise the steps of isolating and restrictively digesting a nucleic acid fragment comprising the nucleic acid sequence encoding the protein of interest, inserting said fragment to a vector, and incorporating the vector into a host cell, whereby copies or clones of said nucleic acid sequence are duplicated in said host cell. However, it may be easier to synthesize the sequence with an automatic nucleotide synthesizer (such as ABI394 DNA synthesizer of Applied Biosystems) according to the nucleotide sequence disclosed herein, or to synthesize separately the fragments of the nucleic acid sequence and to ligate the fragments into a full-length sequence with conventional ligases and vectors using the method of Chinese Patent application 99103472.4, which is disclosed on Oct. 4, 2000.

The nucleic acid sequence of the invention may be genomic, cDNA, RNA, semi-synthesized, completely synthesized sequence, or any combination thereof.

Another aspect of the invention relates to an isolated nucleic acid sequence encoding a protein with EPSPS activity and glyphosate tolerance, wherein the protein comprises the amino acid sequence as shown in SEQ ID NO:3.

The invention further relates to an isolated nucleic acid sequence encoding a protein with EPSPS activity and glyphosate tolerance, wherein the amino acid sequence of the protein comprises substitution, deletion and/or addition of one or more amino acid residues in the amino acid sequence of SEQ ID NO:3, while the EPSPS activity and glyphosate tolerance are remained. Said substitution, deletion and/or addition of one or more amino acid residues are within the conventional technique in the art. Such a change of amino acids is preferably a minor change of features which is a conserved amino acid substitution without prominent influence to the folding and/or activity of the protein; a minor deletion of generally about 1–30 amino acids; a minor extension at amino terminus or carboxyl terminus, such as an extension of one methionine residue at the amino terminus; a minor linker peptide in length of, for example about 20–25 residues.

Examples of conserved substitutions are those occured within the following amino acid groups: basic amino acids (e.g. Arg, Lys and His), acidic amino acids (e.g. Glu and Asp), polar amino acids (e.g. Gin and Asn), hydrophobic amino acids (e.g. Leu, Ile and Val), aromatic amino acids (e.g. Phe, Try and Tyr), and small molecular amino acids (e.g. Gly, Ala, Ser, Thr, and Met). Amino acid substitutions which usually do not change a particular activity are known in the art, and have been described by N. Neurath and R. L. Hill, *Protein*, published by New York Academic Press, 1979. The most common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, and reverser substitutions thereof.

To those skilled in the art, it is obvious that such a substitution may occur at regions other than those important for function but produce an active polypeptide. To the polypeptide encoded by the isolated nucleic acid sequence of the invention, the amino acid residues which is important for function and which is thus selected not to be substituted, may be identified by methods known in the art, for example site-directed mutagenesis or alanine scanning mutagenesis (see, e.g. Cunningham and Wells, 1989, *Science* 244: 1081–1085). The latter technique comprises introducing a mutation into each positive-charged residue in the molecule, and determining the glyphosate-tolerant EPSPS activity of the mutated molecule, thereby determining the amino acid residue important for the activity. The site of substrate-enzyme interaction can also be determined by analysis of the 3D structure, which may be determined by techniques such as nuclear magnetic resonance, crystallography or light-affinity label (see, e.g. de Vos et al, 1992, *Science* 255: 306–312; Smith et al, 1992, *J. Mol. Biol* 224: 899–904; Wlodaver et al, 1992, *FEBS Letters* 309: 59–64).

The invention also relates to an amino acid sequence of the homology, such as the homology of at least about 50%, at least about 60%, at least about 65%, preferably at least about 66%, preferably at least about 67%, preferably at least about 68%, preferably at least about 69%, preferably at least about 70%, preferably at least about 71%, preferably at least about 72%, preferably at least about 73%, preferably at least about 74%, preferably at least about 75%, preferably at least about 76%, preferably at least about 77%, preferably at least about 78%, preferably at least about 79%, more preferably at least about 80%, more preferably at least about 81%, more preferably at least about 82%, more preferably at least about 83%, more preferably at least about 84%, more preferably at least about 85%, more preferably at least about 86%, more preferably at least about 87%, more preferably at least about 88%, more preferably at least about 89%, more preferably at least about 90%, more preferably at least about 91%, more preferably at least about 92%, more preferably at least about 93%, more preferably at least about 94%, more preferably at least about 95%, more preferably at least about 96%, more preferably at least about 97%, more preferably at least about 98%, most preferably at least about 99%, with the amino acid sequence as shown in SEQ ID NO:3. Such a sequence is within the scope of the invention provided that a protein comprising said homologous sequence has the glyphosate-tolerant EPSPS activity.

The protein encoded by the isolated nucleic acid sequence according to the invention has at least 20%, preferably at least 40%, more preferably at least 60%, even more preferably at least 80%, even more preferably at least 90%, most preferably at least 100% of the EPSPS activity of the amino acid sequence as shown in SEQ ID NO:3.

The invention also relates to a nucleic acid construct comprising the above-defined nucleic acid sequence, or its coding sequence (e.g. nucleotides 574–1803 of SEQ ID NO:2).

The nucleic acid construct of the invention further comprises a control sequence essential to the expression of aforesaid sequence in a selected host cell. The control sequence is operably linked to the aforesaid isolated nucleic acid sequence in the nucleic acid construct.

The control sequence may be a promoter, including a transcriptional control sequence directing the expression of a polypeptide. The promoter may be any nucleic acid sequence having transcriptional activity in the selected cell, such as a mutated, truncated, or heterozygous promoter. Such a promoter may be obtained from a gene encoding an extracellular or intracellular peptide. Such a polypeptide may be or may not be homologous to the cell. Various promoters used in prokaryotic cells are known in the art.

The control sequence may also be an appropriate transcription terminator sequence, a sequence recognized by a selected host cell to terminate transcription. The terminator sequence is operably linked to the 3' end of the nucleic acid sequence coding for polypeptide. Any terminator which is functional in the selected host cell may be used in the invention.

The control sequence may also be an appropriate leader sequence, a non-translated region of an mRNA important for the translation in cell. The leader sequence is operably linked to the 5' end of the nucleic acid sequence coding for polypeptide. Any leader sequence which is functional in the selected host cell may be used in the invention.

The control sequence may also be a polyadenylation sequence. The sequence is operably linked to the 3' end of the nucleic acid sequence, and when transcribed, is recognized by the cell as a signal to add polyadenosine residue to transcribed MRNA. Any polyadenylation sequence which is functional in the selected host cell may be used in the invention.

The nucleic acid construct may further comprise one or more nucleic acid sequences which encode one or more factors useful in directing the expression of a foreign polypeptide, such as a transcription-activating factor (e.g. a trans-acting factor), a partner protein and a processing protein. Any factor effective in host cells, in particular bacterial cells and plant cells may be used in the invention. The nucleic acid encoding one or more such factors is not always linked in tandem with the nucleic acid encoding a foreign polypeptide.

The nucleic acids and control sequences described above may be joined in a conventional vector, such as a plasmid or a virus, to produce a "recombinant expression vector" according to the invention, using a method well-known to the skilled in the art (see J. Sambrook, E. F. Fritsch and T. Maniatus, 1989, *Molecullar Cloning*, laboratory manual, $2^{th}$ ed, Cold Spring, N.Y.). The vector may have one or more convenient restriction sites. The choice of vector usually depends on the compatibility of a vector and the host cell being used. The vector may be linear or in close circle and it may be autonomously replicable as an extrachromosomal entity, whose replication is independent from the chromosome replication, e.g. a plasmid (an extrachromosomal element), a minichromosome, or an artificial chromosome. The vector may comprise any means for ensuring self-replication. Alternatively, the vector is integrated into the genome and replicated with the chromosome after being introduced into the cell. The vector system may be a single vector or plasmid, or two or more vectors or plasmids (altogether contain the nucleic acid sequence of interest), or a transposon.

For integration into the host cell genome, the vector may comprise additional nucleic acid sequences that direct the integration of said vector into the genome through homologous recombination. The additional nucleic acid sequences enable said vector to integrate into the genome at a precise position. To increase the possibility of integration into a precise position, the integration elements should preferably comprise a sufficient number of nucleic acids, for example 100–1500 base pairs, preferably 400–1500 base pairs, most preferably 800–1500 base pairs, which are highly homologous to the corresponding target sequences thereof to increase the possibility of homologous integration. Said integration element may be any sequence that is homologous to the target sequence in the genome of the cell. Moreover, said integration elements may be non-coding or coding nucleic acid sequences. Alternatively, said vector may integrate into the genome of the cell through non-homologous integration.

In condition of autonomous replication, the vector may further contain an origin of replication enabling said vector to replicate autonomously in bacterial cells and plant cells.

The invention also relates to a recombinant "host cell" comprising the nucleic acid sequence of the invention. The nucleic acid construct or vector comprising the nucleic acid sequence of the invention may be introduced into the host cell, so that the nucleic acid sequence of the invention is integrated into the chromosome or the vector is autonomously replicated, whereby the nucleic acid sequence of the invention is expressed stably by the host cell and makes the host cell glyphosate-tolerant.

The host cell may be a prokaryotic cell such as a bacterial cell, but more preferably a eukaryotic cell such as a plant cell.

The common bacterial cells include the cells of Gram positive bacteria such as *Bacillus*, or the cells of Gram negative bacteria such as *Escherichia* or *Pseudomonas*. In a preferable embodiment, the bacterial host cell is a cell of *E.coli*.

The introduction of a expression vector into a bacterial host cell may be achieved by protoplast transformation (see Chang and Cohen, 1979, General Molecular Genetics 168: 111–115), using competent cells (see Young and Spizizin, 1961, J. Bacteriol. 81: 823–829, or Dubnau and Davidoff-Abelson, 1971, J. Mol. Biol. 56: 209–221), electroporation (see Shigekawa and Dower, 1988, Biotech. 6: 742–751), or conjugation (see Koehler and Thorne, 1987, J. Bacteriol. 169: 5771–5278).

DESCRIPTION OF FIGURES

FIG. 1 shows the map of plasmid pKU2004.

FIG. 2 shows the amino acid sequence alignment between EPSPS of *Pseudomonas putida* P. P4G-1 (SEQ ID NO:3) with various known EPSPSs SEQ ID NOs 13–19, 12, and 20–25 respectively. Sequences shown in box and shade are claimed in previous patents.

FIG. 3 shows the growth curve of *E.coli* XL1-BLUE MR in different glyphosate concentrations. Said *E.coli* XL1-BLUE MR carries different EPSPS genes.

EXAMPLES

Example 1

Isolation of Gylphosate-Tolerant Strains

The sample were taken from neighborhood of a glyphosate producing factory in Hebei Province, China, and were diluted and spread on mediums comprising glyphosate. A total of 48 strains are isolated with high tolerance and degradation ability to glyphosate. One strain of them, 4G-1, is able to grow on a medium with 400 mM glyphosate, and is resistant to 100 mg/L Ampicillin. Said strain is selected for further studies.

Example 2

Identification of Glyphosate-Tolerant Strains a) Mini-Prep of the Total DNA of Strain 4G-1

Strain 4G-1 is inoculated in 3 ml of LB liquid medium with 100 mg/L Ampicillin, and cultured at 28° C. overnight while shaking. The culture is centrifuged at 12000 rpm and the pellet is resuspended in 0.5 ml of Solution I (10 mM NaCl, 20 mM Tris-Hcl pH 8.0, 1 mM EDTA). Protease K (Merck, Germany) and SDS are added to a final concentration of 10 μg/ml and 0.5%, respectively. The suspension is then mixed by careful reversion, and then left at 50° C. for more than 6 hrs. An equal volume of phenol is added. The mixture is carefully reversed and left at room temperature for 10 min. Then, the mixture is centrifuged at 12000 rpm at room temperature for 5 min. The supernatant aqueous phase is drawn out with tips (Axy Gen, USA), and the pellet is reextracted with equal volume of phenol/chloroform. The supernatant is added with 10% of 3M NaAC and 2.3 volume of ethanol for precipitation. The mixture is centrifuged at 12000 rpm at −10° C. for 25 min. After the supernatant is discarded, the precipitate is washed with 500 μl of 70% ethanol and centrifuge at 12000 rpm for 1 min. After the supernatant is drawn off completely, the precipitate is dried in Savant for 20 min or in the incubator at 37° C. for 1 hr. The precipitate is added with 100 μl of TE solution (10 mM Tris-Cl, 1 mM EDTA, pH 8.0) for solubilization, then frozen at −20° C. for further studies.

b) Cloning of 16S rRNA of Strain 4G-1

A pair of universal primers of 16S rRNA (primer 1:5' AGAGTTTG ACATGGCTCAG 3' (SEQ ID NO:4) and primer 2:5' TACGGTTACCTTGTTACGACTT 3' (SEQ ID NO:5)) is synthesized. The PCR amplification reaction is run in the Robocycler 40 (Stratagene) using the primers. The reaction system is: 1 μl of total DNA of strain 4G-1 as template, 5 μl of buffer, 4 μl of 10 μmol dNTP, 1 μl of 20 pmol/μl primer 1, 1 μl of 20 pmol/μprimer 2 and 37 μl of deionized water. The reaction condition is: 94° C. 10 min, with 1 μl of 5U Pyrobest Taq DNA polymerase added, then 94° C. 1 min, 50° C. 1 min, 72° C. 2 min for 30 circles, and finally extended at 72° C. for another 10 min. A fragment of about 1.5 kb is obtained. The PCR product is purified according to the method provide by the manufacturer of the PCR product purification kit, Boehringer.

The purified PCR product is subjected to poly-A (deoxyadenosine) reaction. The reaction system is: 20 μl (2 μg) of purified PCR product, 5 μl of buffer, 1 μl (5U) of Taq DNA polymerase (DingGuo Ltd, Beijing), 4 μl of 5 μmol dATP and 20 μl of deionized water.

The resulting products are purified by a purification method for PCR product, and are ligated to a T vector (Takara, Dalian) according to the instruction of manufacturer Takara to obtain plasmid pKU2000. The result of sequencing shows in SEQ ID NO: 1. Using BLAST software and BLASTP 2.2.2 [Dec. 14-2001] database for sequence alignment in the American National Center for Biotechnology Information (NCBI), it is found that said sequence is 99% homologous to the nucleotide sequence of 16S rRNA of *Pseudomonas putida*. Thus, strain 4G-1 is thought to be *P. putida*, and is designated as *P. putida* 4G-1 (abbreviated as P. P4G-1). Said strain is deposited on Apr. 30, 2002 at the Chinese General Microbiological Culture Centre (CGMCC) (ZhongGuan Cun, Beijing, China) with the accession number CGMCC 0739.

Example 3

Construction of the Genomic Library of Strain 4G-1 a) Maxi-prep of the Total DNA of 4G-1

The strain P. P4G-1 is inoculated into 100 ml of LB medium (supplemented with 100 mg/L Ampicillin) in a 250 ml flask, and cultured at 28° C. overnight while shaking at 200 rpm. The culture is centrifuged at 8000 rpm for 5 min, then the pellet is resuspended in 14 ml of Solution I. Protease K (Merck, Germany) and SDS are added to a final concentration of 10 μg/ml and 0.5%, respectively. The mixture is mixed by careful reversion and left at 50° C. for more than 6 hr. An equal volume of phenol is added. The mixture is carefully reverted and left at room temperature for 10 min. The mixture is centrifuged in room temperature at 4000 rpm for 20 min. The supernatant aqueous phase is-drawn with wide-end tips, and extracted with equal volume of phenol/chloroform. The supernatant is added with 10% of 3M NaAC (pH 5.5) and 2.3 volume of ethanol for precipitation. The DNA is carefully picked out using a glass rod and washed in 70% ethanol. After ethanol is discarded, the DNA is dried. 2 ml of TE solution (pH 8.0) at 4° C. is added for solubilization for 24 hr and about 1 mg of total DNA is obtained. The DNA fragment is identified to be more than 80 Kb using 0.3% agarose gel electrophoresis.

b) Recovery of the Digestive Products of Total DNA

200 μl of total DNA (100 μg) is digested with 5U of restriction endonuclease Sau3AI at room temperature for 20 min, 30 min and 45 min, respectively. The products are combined and added with EDTA to a final concentration of 0.25 mM, and then extracted with equal volume of phenol/chloroform. The supernatant is added with 10% of 3M NaAC and 2.3 volume of ethanol for precipitation. The precipitate is washed with 70% ethanol, and dried as mentioned above. Then the precipitate is solubilized in 200 μl of TE, and loaded on 12 ml of 10–40% sucrose density gradient in a Beckman sw28 ultra centrifuge tube. The samples is place in the Beckman sw28 roter at 20° C. and centrifuged at 120000 g for 18 hrs. Each fraction is collected from the top (0.5 ml) and 15 μl aliquot is analyzed by 0.3% agarose gel electrophoresis. The bands comprising the DNA of 30–40 kb are combined, added with about 2 volumes of deionized water and 7 volumes of ethanol for precipitated at −20° C. overnight, then washed with 70% ethanol, dry and solubilized in 50 μl of TE.

c) Construction of Genomic Library of 4G-1

SuperCos1 cosmid vector is digested with Xba I, alkaline phosphatase and BamHI, then ligated with the isolated total DNA fragments described above, using the method of Stratagne.

The package extract of Gigapack III Gold is used to pack a ligation product in vitro. The library is titrated with a Stratagene kit on *E.coli* XL1-Blue MR (Stratagene), using the method of Stratagne. The obtained library is then amplified and stored according to the instruction of the same manufacturer.

Example 4

Isolation, Screening, Sequencing and Analysis of a Glyphosate-Tolerant EPSPS Gene a) Screen of the Glyphosate-Tolerant Gene Library 1 ml stock solution of the library described above is centrifuged, the supernatant is discarded and the pellet is resuspend in 1 ml sterile saline. Centrifuge is repeated again and the supernatant is discarded, the pellet is resuspend in 1 ml sterile saline. The suspension is spreaded onto the 10 mM glyphosate-50 mg/L Ampicillin plate (20 mM ammonium sulfate; 0.4% glucose; 10 mM glyphosate; 0.5 mM dipotassium hydrogen phosphate; 0.1 mg/L ferric sulfate; 0.5 g/L magnesium sulfate; 0.5 g/L calcium chloride; 2.1 g/L sodium chloride; 50 mM Tris (pH 7.2); 5 mg/L Vitamin B1; 15 g/L agarose) in a density of about $10^3$ bacteria/plate. The plate is cultured overnight at 37° C. One strain is obtained and designated as BDS. The cosmid carried by the strain is designated as pKU2001.

b) Isolation of the Glyphosate-Tolerant Gene

The strain BDS is inoculated in 20 ml of LB (supplemented with 50 mg/L Ampicillin) in a 50 ml flask, and cultured at 37° C. for 12 hr while shaking at 300 rpm. The strain is collected after centrifugation. The plasmid pKU2001 is extracted by an alkaline method according to *Molecullar cloning, laboratory manual*, supra. This plasmid is then transformed into *E.coli* XL1-Blue MR (Stratagene) along with a cosmid vector. The strains are streaked on 10 mM glyphosate plate. Those merely carrying the empty cosmid vector is not able to grown on the glyphosate medium, while those carrying pKU2001 grows well, indicating that pKU2001 carries the glyphosate-tolerant gene.

The pKU2001 is digested with Sau3AI. A DNA fragment of 2–4 kb is recovered using 0.7% agarose gel electrophoresis, and ligated to the BamH I-digested and dephosphorylated pUC18 vector (Yanisch-Perron, C., Vieria, J. and Messing, J. 1985, Gene 33:103–119). The ligation is transformed into *E.coli* XL1-Blue MR (Stratagene) and the strain is streaked on the 10 mM glyphosate plate supplemented with 50 mg/L Ampicillin. The plates are cultured overnight at 37° C. and dozens of clones are obtained. The clones are picked up and plasmids are extracted. A plasmid carrying an exogenous fragment of about 2 kb is screened out and designated as pKU2002. The plasmid pKU2002 and the empty vector pUC18 are transformed into *E.coli* XL1-Blue MR (Stratagene) respectively. Strains are streaked on the 10 mM glyphosate plates with 50 μg/ml Ampicillin. Those carrying pUC18 empty vector are not able to grow on the glyphosate plate, while those carrying pKU2002 plasmid grows well, indicating that the plasmid pKU2002 carries glyphosate resistant gene.

c) pKU2002 is sequenced, and a full-length sequence of 1914 bp is obtained as shown in SEQ ID NO:2.

d) pKU2002 is subjected to sequence analysis using DNASIS software. The unique possible open reading frame (ORF, nucleotides 574–1803 of SEQ ID NO:2) is determined. The amino acid sequence encoded is shown in SEQ ID NO:3.

e) The protein sequence is subjected to BLAST search in the GenBank protein sequence database of American National Center for Biotechnology Information (NCBI). It is found that the sequence of the protein is 37% homologous to the amino acid sequence of EPSPS of *Clostridium acetobutylicum*, and is 20% homologous to the amino acid sequence of EPSPS of *E.coli*. The 1230 bp sequence is thought to encode an EPSP synthase, and the gene is designated as pparoA. Analysis shows that said gene does not belong to any class of EPSPS, it is a novel EPSPS gene (Class III). The EPSPS amino acid sequence alignment of *E.coli*, *Clostridium acetobutylicum* and P. P4G-1 is shown in FIG. 2.

f) A pair of primers is designed comprising a BamH I site shown as underlined:

```
Primer 3: 5'-CGGGATCCTAAGTAAGTGAAAGTAACAATACAGC-3'  (SEQ ID NO:6)

Primer 4: 5'-CGGGATCCCTTCTTCGGACAATGACAGAC-3'       (SEQ ID NO:7)
```

The PCR amplification is run with pKU2001 the template. The amplified fragment is digested with BamHI and inserted into pUC18 to obtain plasmid pKU2003. Sequencing shows that no mismatching base is introduced. pKU2003 is digested with BamHI and ligated into the BamHI site of pACYC184 in a forward direction (Chang, A. C. Y., and Cohen, S. N., 1978, J. Bacteriol. 134: 1141–1156) to obtain plasmid pKU2004, the map of which is shown in FIG. 1. The transcription of pparoA gene in this plasmid is initiated by the promoter Tc$^r$ derived from pACYC184.

Example 5

Cloning of *E.coli* aroA Gene and Site-Directed Mutagenesis of its Glyphosate Tolerance (Control Test)

The *E.coli* ET8000 (MacNeil, T., MacNeil, D., and Tyler, B. 1982 J. Bacteriol. 150: 1302–1313) is inoculated into 3 ml of LB liquid medium in a 15 ml tube, and cultured with shaking at 37° C. overnight. The strain is centrifuged, and total DNA is extracted according to the method described above.

A pair of primers is designed to include a BamHI site shown as underlined:

The *E.coli* aroA gene which encodes EPSPS protein in *E.coli* is obtained by amplification using the total DNA of *E.coli* as template. Said gene is digested with BamHI and inserted into pUC18 to obtain the plasmid pKU2005. The sequence of the plasmid is analyzed and SEQ ID NO:10 is obtained. The sequence is proved to be correct after alignment with the known EPSPS gene sequence of *E.coli* in the GenBank data of NCBI. After digesting the plasmid pKU2005 with BamHI the small fragment is recovered and inserted in forward direction into the BamHI site of pACYC184, and the plasmid pKU2006 is obtained.

The aroA gene of *E.coli* is subjected to site mutation. The Guanine on site 287 is mutated to Cytosine. Then the Glycine on site 96 of the *E.coli* EPSPS protein is mutated to Alanine. Similarly, said gene fragment is inserted into the BamHI site of pACYC184 to obtain plasmid pKU2007.

Example 6

The EPSPS Function-Complementation Experiment of *E.coli* aroA$^{-Strain}$ pACYC184, pKU2004, pKU2006 and pKU2007 are transformed into *E.coli* AB2889 (*E.coli* aroA$^-$ strain, from Yale University) respectively. They are streaked on M63 medium (13.6 g/L KH$_2$PO$_4$, 0.5 mg/L FeSO$_4$·7H$_2$O, 20 mM (NH$_4$)$_2$SO$_4$, 0.4% glucose, 1 mM magnesium sulfate, 0.5 mg/L Vitamin B1) comprising chloroamphenicol in a final concentration of 25 mg/L for culture. The results are shown in Table 1.

The aAAS components are supplemented as follows:

| | |
|---|---|
| 100 mg/L | Phenylanine |
| 100 mg/L | Tyrosine |
| 100 mg/L | Tryptophane |
| 5 mg/L | p-aminobenzoic acid |
| 5 mg/L | 2,3-dihydroxybenzoic acid |
| 5 mg/L | p-hydroxybenzoic acid |

TABLE 1

The experiments of EPSPS function-complementation and glyphosate tolerance of aroA-deficient *E. coli* strain

| the plasmid carried by AB2889 | EPSPS function-complementation and glyphosate tolerance | | |
|---|---|---|---|
| | M63 medium | M63 medium (supp. aAAS) | 10 mM glyphosate tolerance |
| pACYC184 | − | + | − |
| PKU2006 | + | + | − |
| pKU2007 | + | + | + |
| pKU2004 | + | + | + |

```
Primer 5: 5'-CGGGATCCGTTAATGCCGAAATTTTGCTTAATC-3'  (SEQ ID NO:8)

Primer 6: 5'-CGGGATCCAGGTCCGAAAAAAAACGCCGAC-3'     (SEQ ID NO:9)
```

At the same time, the growth curves of the strains are measured in liquid culture condition. The results show that, as same as the control aroA gene of *E.coli* (pKU2006), the gene carried by pKU2004 is able to completely complement the EPSPS function of aroA deficient *E.coli* AB2899, suggesting that the 1230-bp nucleic acid sequence carried by said plasmid is a EPSPS encoding gene, and the EPSPS encoded by said gene has glyphosate tolerance.

Example 7

The Glyphosate Tolerance of the Novel EPSPS Gene

The plasmids pKU2004, pKU2006 and pKU2007 are transformed into the *E.coli* XL1-Blue MR, respectively. Stains are inoculated and cultured overnight on M63 mediums separately, and then transferred to M63 mediums supplemented with different concentrations of glyphosate. The growth curves are measured. The results show that the *E.coli* transformed with pKU2006 is inhibited significantly when growing in the 5 mM glyphosate medium, and does not grow in the 40 mM glyphosate medium. In constrast, the *E.coli* transformed with pKU2004 and pKU2006 are not inhibited obviously when growing in the 40 mM glyphosate medium, and the *E.coli* transformed with pKU2004 grows well in 120 mM glyphosate medium (FIG. 3: growth curve).

What is claimed is:

1. An isolated nucleic acid encoding a glyphosate tolerant 5-enolpyruvylshikimate-3-phosphate synthase (EPSPS), wherein the synthase is characterized by that it:
    (i) comprises the amino acid sequence shown in SEQ ID NO:3, or
    (ii) is the glyphosate tolerant 5-enolpyruvylshikimate-3-phosphate synthase (EPSPS) which is modified by substitution, deletion or addition of one or more amino acids to the amino acid sequence of (i) and is at least 95% identical to SEQ ID NO: 3.

2. The isolated nucleic acid according to claim 1, characterized by that it:
    (i) comprises the sequence shown in nucleotides 574–1803 of SEQ ID NO:2, or
    (ii) comprises the nucleotide sequence which is modified by substitution of one or more nucleotides, or the deletion or addition of three or a multiple of three nucleotides to the nucleotide sequence of (i), and the protein encoded by said nucleotide sequence has the activity of glyphosate tolerant 5-enolpyruvylshikimate-3-phosphate synthase (EPSPS) and the glyphosate tolerance.

3. A nucleic acid construct, which comprises the isolated nucleic acid according to claim 1.

4. A vector, which carries the isolated nucleic acid according to claim 1.

5. A host cell, which is transformed by the nucleic acid construct according to claim 3.

6. A host cell or progeny cell hereof, wherein said cell contains the isolated nucleic acid according to claim 1 and has the glyphosate tolerance.

7. A host cell or progeny cell hereof, wherein said cell contains the isolated nucleic acid according to claim 2 and has the glyphosate tolerance.

8. A method for preparing a host cell, comprising operably linking the nucleic acid of claim 1 with appropriate control sequences, introducing them into an appropriate vector, introducing said vector into a selected host cell, and expressing an active glyphosate tolerant 5-enolpyruvylshikimate-3-phosphate synthase (EPSPS) encoded by the nucleic acid sequence.

9. A nucleic acid construct, which comprises the isolated nucleic acid according to claim 2.

10. A vector, which carries the isolated nucleic acid according to claim 2.

11. A vector, which carries the nucleic acid construct according to claim 3.

12. A vector, which carries the nucleic acid construct according to claim 9.

13. A host cell, which is transformed by the nucleic acid construct according to claim 9.

14. A host cell, which is transformed by the nucleic acid construct according to claim 4.

15. A host cell, which is transformed by the nucleic acid construct according to claim 10.

16. A host cell, which is transformed by the nucleic acid construct according to claim 11.

17. A host cell, which is transformed by the nucleic acid construct according to claim 12.

18. The isolated nucleic acid according to claim 1, wherein the nucleic acid encodes a polypeptide that is at least 96% identical to SEQ ID NO: 3.

19. The isolated nucleic acid according to claim 2, characterized by that it:
    (i) comprises the nucleotide sequence shown in SEQ ID NO:2, or
    (ii) comprises the nucleotide sequence which is modified by substitution of one or more nucleotides, or the deletion or addition of three or a multiple of three nucleotides to the nucleotide sequence of (i), and the protein encoded by said nucleotide sequence has the activity of glyphosate tolerant 5-enolpyruvylshikimate-3-phosphate synthase (EPSPS) and the glyphosate tolerance.

20. The isolated nucleic acid according to claim 2, wherein the nucleic acid is at least 65% identical to nucleotides 574–1803 of SEQ ID NO: 2.

21. The isolated nucleic acid according to claim 20, wherein the nucleic acid is at least 95% identical to nucleotides 574–1803 of SEQ ID NO: 2.

22. The isolated nucleic acid according to claim 2, wherein the nucleic acid is at least 65% identical to SEQ ID NO: 2.

23. The isolated nucleic acid according to claim 22, wherein the nucleic acid is at least 95% identical to SEQ ID NO: 2.

* * * * *

SEQUENCE LISTING

```
<160> NUMBER OF SEQ ID NOS: 25

<210> SEQ ID NO 1
<211> LENGTH: 1501
<212> TYPE: DNA
<213> ORGANISM: Pseudomonas putida P.P4G-1

<400> SEQUENCE: 1
agagtttgat catggctcag attgaacgct ggcggcaggc ctaacacatg caagtcgagc      60
ggatgagaag agcttgctct tcgattcagc ggcggacggg tgagtaatgc ctaggaatct     120
gcctggtagt gggggacaac gtttcgaaag gaacgctaat accgcatacg tcctacggga     180
gaaagcaggg gaccttcggg ccttgcgcta tcagatgagc ctaggtcgga ttagctagtt     240
ggtgaggtaa tggctcacca aggcgacgat ccgtaactgg tctgagagga tgatcagtca     300
cactggaact gagacacggt ccagactcct acgggaggca gcagtgggga atattggaca     360
atgggcgaaa gcctgatcca gccatgccgc gtgtgtgaag aaggtcttcg gattgtaaag     420
cactttaagt tgggaggaag ggcattaacc taatacgtta gtgttttgac gttaccgaca     480
gaataagcac cggctaactc tgtgccagca gccgcggtaa tacagagggt gcaagcgtta     540
atcggaatta ctgggcgtaa agcgcgcgta ggtggtttgt taagttggat gtgaaagccc     600
cgggctcaac ctgggaactg tatccaaaac tggcaagcta gagtacggta gagggtggtg     660
gaatttcctg tgtagcggtg aaatgcgtag atataggaag gaacaccagt ggcgaaggcg     720
accacctgga ctgatactga cactgaggtg cgaaagcgtg gggagcaaac aggattagat     780
accctggtag tccacgccgt aaacgatgtc aactagccgt tggaatcctt gagattttag     840
tggcgcagct aacgcattaa gttgaccgcc tggggagtac ggccgcaagg ttaaaactca     900
aatgaattga cggggcccg cacaagcggt ggagcatgtg gtttaattcg aagcaacgcg     960
aagaacctta ccaggccttg acatgcagag aactttccag agatggattg gtgccttcgg    1020
gaactctgac acaggtgctg catggctgtc gtcagctcgt gtcgtgagat gttgggttaa    1080
gtcccgtaac gagcgcaacc cttgtcctta gttaccagca cgtaatggtg ggcactctaa    1140
ggagactgcc ggtgacaaac cggaggaagg tggggatggc gtcaagtcat catggcccctt   1200 acggcctggg ctacacacgt gctacaatgg tcggtacaga gggttgccaa gccgcgaggt    1260
ggagctaatc tcacaaaacc gatcgtagtc cggatcgcag tctgcaactc gactgcgtga    1320
agtcggaatc gctagtaatc gcgaatcaga atgtcgcggt gaatacgttc ccgggccttg    1380
tacacaccgc ccgtcacacc atgggagtgg gttgcaccag aagtagctag tctaaccttc    1440
```

```
gggaggacgg ttaccacggt gtgattcatg actggggtga agtcgtaaca aggtaaccgt    1500
a                                                                   1501

<210> SEQ ID NO 2
<211> LENGTH: 1914
<212> TYPE: DNA
<213> ORGANISM: Pseudomonas putida P.P4G-1
<220> FEATURE:
<221> NAME/KEY: CDS
<222> LOCATION: (574)...(1800)

<400> SEQUENCE: 2
gatcataaaa catgcttgta taaaggatgc tgccatgttc cgtgaactgg aagcgaacaa     60
tcttgcggta tatcagaaaa agccaaagct gattgcagtg cttcttcagc gtaatgctca    120
gttaaaagcg aaggttgttc aggaggatga gttcgaaaag tcggtaaggc gtttgttgaa    180 cttggtcat acattgggc atgccatcga aatgaatat gcgttgatgc atggccatgc       240
ggttgctata ggaatgacat acgcgtgtca tatttctgag caattgtctg gattcaaaca    300
aacaaatcgc gtggtagaag tgttggaaca atatgggtta ccgacttata tggcattcga    360
tagggaaaag gcttttaatc tgttgaaaat ggacaagaag cgtgaaaaaa aggaaatgaa    420
ctatgtgttg ctggaaaaag tagggaaggg agtggtgaag agtattccac tggttcaatt    480
agaaaaaatc attcaagcat taccaaagtg aaagtaacaa tacagcccgg agatctgact    540
ggaattatcc agtcacccgc ttcaaaaagt tcg atg cag cga gct tgt gct gct     594
                                    Met Gln Arg Ala Cys Ala Ala
                                    1               5 gca ctg gtt gca aaa gga ata agt gag atc att aat ccc ggt cat agc      642
Ala Leu Val Ala Lys Gly Ile Ser Glu Ile Ile Asn Pro Gly His Ser
     10                  15                  20 aat gat gat aaa gct gcc agg gat att gta agc cgg ctt ggt gcc agg      690
Asn Asp Asp Lys Ala Ala Arg Asp Ile Val Ser Arg Leu Gly Ala Arg
 25                  30                  35 ctt gaa gat cag cct gat ggt tct ttg cag ata aca agt gaa ggc gta      738
Leu Glu Asp Gln Pro Asp Gly Ser Leu Gln Ile Thr Ser Glu Gly Val
40                  45                  50                  55 aaa cct gtc gct cct ttt att gac tgc ggt gaa tct ggt tta agt atc     786
Lys Pro Val Ala Pro Phe Ile Asp Cys Gly Glu Ser Gly Leu Ser Ile
                 60                  65                  70 cgg atg ttt act ccg att gtt gcg ttg agt aaa gaa gag gtg acg atc     834
Arg Met Phe Thr Pro Ile Val Ala Leu Ser Lys Glu Glu Val Thr Ile
             75                  80                  85 aaa gga tct gga agc ctt gtt aca aga cca atg gat ttc ttt gat gaa     882
Lys Gly Ser Gly Ser Leu Val Thr Arg Pro Met Asp Phe Phe Asp Glu
         90                  95                 100 att ctt ccg cat ctc ggt gta aaa gtt aaa tct aac cag ggt aaa ttg     930
Ile Leu Pro His Leu Gly Val Lys Val Lys Ser Asn Gln Gly Lys Leu
    105                 110                 115 cct ctc gtt ata cag ggg cca ttg aaa cca gca gac gtt acg gtt gat     978
Pro Leu Val Ile Gln Gly Pro Leu Lys Pro Ala Asp Val Thr Val Asp
120                 125                 130                 135 ggg tcc tta agc tct cag ttc ctt aca ggt ttg ttg ctt gca tat gcg    1026
Gly Ser Leu Ser Ser Gln Phe Leu Thr Gly Leu Leu Leu Ala Tyr Ala
                140                 145                 150 gcc gca gat gca agc gat gtt gcg ata aaa gta acg aat ctc aaa agc    1074
Ala Ala Asp Ala Ser Asp Val Ala Ile Lys Val Thr Asn Leu Lys Ser
            155                 160                 165 cgt ccg tat atc gat ctt aca ctg gat gtg atg aag cgg ttt ggt ttg    1122
```

```
                Arg Pro Tyr Ile Asp Leu Thr Leu Asp Val Met Lys Arg Phe Gly Leu
                        170                 175                 180 aag act ccc gag aat cga aac tat gaa gag ttt tat ttc aaa gcc ggg         1170
Lys Thr Pro Glu Asn Arg Asn Tyr Glu Glu Phe Tyr Phe Lys Ala Gly
        185                 190                 195 aat gta tat gat gaa acg aaa atg caa cga tac acc gta gaa ggc gac         1218
Asn Val Tyr Asp Glu Thr Lys Met Gln Arg Tyr Thr Val Glu Gly Asp
200                 205                 210                 215 tgg agc ggt ggt gct ttt tta ctg gta gcg ggg gct att gcc ggg ccg         1266
Trp Ser Gly Gly Ala Phe Leu Leu Val Ala Gly Ala Ile Ala Gly Pro
                220                 225                 230 atc acg gta aga ggt ttg gat ata gct tcg acg cag gct gat aaa gcg         1314
Ile Thr Val Arg Gly Leu Asp Ile Ala Ser Thr Gln Ala Asp Lys Ala
        235                 240                 245 atc gtt cag gct ttg atg agt gcg aac gca ggt att gcg att gat gca         1362
Ile Val Gln Ala Leu Met Ser Ala Asn Ala Gly Ile Ala Ile Asp Ala
250                 255                 260 aaa gag atc aaa ctt cat cct gct gat ctc aat gca ttt gaa ttt gat         1410
Lys Glu Ile Lys Leu His Pro Ala Asp Leu Asn Ala Phe Glu Phe Asp
                265                 270                 275 gct act gat tgc ccg gat ctt ttt ccg cca ttg gtt gct ttg gcg tct         1458
Ala Thr Asp Cys Pro Asp Leu Phe Pro Pro Leu Val Ala Leu Ala Ser
280                 285                 290                 295 tat tgc aaa gga gaa aca aag atc aaa ggc gta agc agg ctg gcg cat         1506
Tyr Cys Lys Gly Glu Thr Lys Ile Lys Gly Val Ser Arg Leu Ala His
                300                 305                 310 aaa gaa agt gac aga gga ttg acg ctg cag gac gag ttc ggg aaa atg         1554
Lys Glu Ser Asp Arg Gly Leu Thr Leu Gln Asp Glu Phe Gly Lys Met
        315                 320                 325 ggt gtt gaa atc cac ctt gag gga gat ctg atg cgc gtg atc gga ggg         1602
Gly Val Glu Ile His Leu Glu Gly Asp Leu Met Arg Val Ile Gly Gly
330                 335                 340 aaa ggc gta aaa gga gct gaa gtt agt tca agg cac gat cat cgc att         1650
Lys Gly Val Lys Gly Ala Glu Val Ser Ser Arg His Asp His Arg Ile
                345                 350                 355 gcg atg gct tgc gcg gtg gct gct tta aaa gct gtg ggt gaa aca acc         1698
Ala Met Ala Cys Ala Val Ala Ala Leu Lys Ala Val Gly Glu Thr Thr
360                 365                 370                 375 atc gaa cat gca gaa gcg gtg aat aaa tcc tac ccg gat ttt tac agc         1746
Ile Glu His Ala Glu Ala Val Asn Lys Ser Tyr Pro Asp Phe Tyr Ser
                380                 385                 390 gat ctt aaa caa ctt ggc ggt gtt gta tct tta aac cat caa ttt aat         1794
Asp Leu Lys Gln Leu Gly Gly Val Val Ser Leu Asn His Gln Phe Asn
        395                 400                 405 ttc tca tgaatagctt cggccgcatc ttcagggtgc atattttgg cgaatcacat          1850
Phe Ser ggtgaatcag taggcatcgt tattgatggt tgtcctgctg gtctgtcatt gtccgaagaa      1910
gatc                                                                   1914

<210> SEQ ID NO 3
<211> LENGTH: 409
<212> TYPE: PRT
<213> ORGANISM: Pseudomonas putida P.P4G-1

<400> SEQUENCE: 3

Met Gln Arg Ala Cys Ala Ala Ala Leu Val Ala Lys Gly Ile Ser Glu
1               5                   10                  15

Ile Ile Asn Pro Gly His Ser Asn Asp Asp Lys Ala Ala Arg Asp Ile
            20                  25                  30
```

-continued

```
Val Ser Arg Leu Gly Ala Arg Leu Glu Asp Gln Pro Asp Gly Ser Leu
        35                  40                  45

Gln Ile Thr Ser Glu Gly Val Lys Pro Val Ala Pro Phe Ile Asp Cys
    50                  55                  60

Gly Glu Ser Gly Leu Ser Ile Arg Met Phe Thr Pro Ile Val Ala Leu
65                  70                  75                  80

Ser Lys Glu Glu Val Thr Ile Lys Gly Ser Gly Ser Leu Val Thr Arg
                85                  90                  95

Pro Met Asp Phe Phe Asp Glu Ile Leu Pro His Leu Gly Val Lys Val
            100                 105                 110

Lys Ser Asn Gln Gly Lys Leu Pro Leu Val Ile Gln Gly Pro Leu Lys
        115                 120                 125

Pro Ala Asp Val Thr Val Asp Gly Ser Leu Ser Ser Gln Phe Leu Thr
    130                 135                 140

Gly Leu Leu Leu Ala Tyr Ala Ala Asp Ala Ser Asp Val Ala Ile
145                 150                 155                 160

Lys Val Thr Asn Leu Lys Ser Arg Pro Tyr Ile Asp Leu Thr Leu Asp
                165                 170                 175

Val Met Lys Arg Phe Gly Leu Lys Thr Pro Glu Asn Arg Asn Tyr Glu
            180                 185                 190

Glu Phe Tyr Phe Lys Ala Gly Asn Val Tyr Asp Glu Thr Lys Met Gln
        195                 200                 205

Arg Tyr Thr Val Glu Gly Asp Trp Ser Gly Gly Ala Phe Leu Leu Val
    210                 215                 220

Ala Gly Ala Ile Ala Gly Pro Ile Thr Val Arg Gly Leu Asp Ile Ala
225                 230                 235                 240

Ser Thr Gln Ala Asp Lys Ala Ile Val Gln Ala Leu Met Ser Ala Asn
                245                 250                 255

Ala Gly Ile Ala Ile Asp Ala Lys Glu Ile Lys Leu His Pro Ala Asp
            260                 265                 270

Leu Asn Ala Phe Glu Phe Asp Ala Thr Asp Cys Pro Asp Leu Phe Pro
        275                 280                 285

Pro Leu Val Ala Leu Ala Ser Tyr Cys Lys Gly Glu Thr Lys Ile Lys
    290                 295                 300

Gly Val Ser Arg Leu Ala His Lys Glu Ser Asp Arg Gly Leu Thr Leu
305                 310                 315                 320

Gln Asp Glu Phe Gly Lys Met Gly Val Glu Ile His Leu Glu Gly Asp
                325                 330                 335

Leu Met Arg Val Ile Gly Gly Lys Gly Val Lys Gly Ala Glu Val Ser
            340                 345                 350

Ser Arg His Asp His Arg Ile Ala Met Ala Cys Ala Val Ala Ala Leu
        355                 360                 365

Lys Ala Val Gly Glu Thr Thr Ile Glu His Ala Glu Ala Val Asn Lys
    370                 375                 380

Ser Tyr Pro Asp Phe Tyr Ser Asp Leu Lys Gln Leu Gly Gly Val Val
385                 390                 395                 400

Ser Leu Asn His Gln Phe Asn Phe Ser
                405
```

<210> SEQ ID NO 4
<211> LENGTH: 20
<212> TYPE: DNA
<213> ORGANISM: Artificial Sequence
<220> FEATURE:

```
<223> OTHER INFORMATION: Primer

<400> SEQUENCE: 4
agagtttgat catggctcag                                               20

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
tacggttacc ttgttacgac tt                                            22

<210> SEQ ID NO 6
<211> LENGTH: 34
<212> TYPE: DNA
<213> ORGANISM: Artificial Sequence
<220> FEATURE:
<223> OTHER INFORMATION: Primer

<400> SEQUENCE: 6
cgggatccta agtaagtgaa agtaacaata cagc                               34

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
cgggatcccT tcttcggaca atgacagac                                     29

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
cgggatccgt taatgccgaa attttgctta atc                                33

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
cgggatccag gtccgaaaaa aaacgccgac                                    30

<210> SEQ ID NO 10
<211> LENGTH: 1436
<212> TYPE: DNA
<213> ORGANISM: Escherichia coli

<400> SEQUENCE: 10
gttaatgccg aaattttgct taatccccac agccagcctg tggggttttt atttctgttg     60
tagagagttg agttcatgga atccctgacg ttcaacccca tcgctcgtgt cgatggcact    120
attaatctgc ccggttccaa gagcgtttct aaccgcgctt tattgctggc ggcattagca    180
```

-continued

```
cacggcaaaa cagtattaac caatctgctg gatagcgatg acgtgcgcca tatgctgaat    240
gcattaacag cgttaggggt aagctatacg ctttcagccg atcgtacgcg ttgcgaaatt    300
atcggtaacg gcggtccatt acacgcagaa ggtgccctgg agttgttcct cggtaacgcc    360
ggaacggcaa tgcgtccgct ggcggcagct ctttgtctgg gtagcaatga tattgtgctg    420
accggtgagc gcgtatgaa agaacgcccg attggtcatc tggtggatgc gctgcgcctg    480
ggcggggcga agatcactta cctggaacaa gaaaattatc cgccgttgcg tttacagggc    540
ggctttactg cggcaacgt tgacgttgat ggctccgttt ccagccaatt cctcaccgca    600
ctgttaatga ctgcgcctct tgcgccggaa gatacggtga ttcgtattaa aggcgatctg    660
gtttctaaac cttatatcga catcacactc aatctgatga agacgtttgg tgttgaaatt    720
gaaaatcagc actatcaaca atttgtcgta aaaggcgggc agtcttatca gtctccgggt    780
acttatttgg tcgaaggcga tgcatcttcg gcttcttact ttctggcagc agcagcaatc    840
aaaggcggca ctgtaaaagt gaccggtatt ggacgtaaca gtatgcaggg tgatattcgc    900
tttgctgatg tgctggaaaa aatgggcgcg accatttgct ggggcgatga ttatatttcc    960
tgcacgcgtg gtgaactgaa cgctattgat atggatatga accatattcc tgatgcggcg    1020
atgaccattg ccacggcggc gttatttgca aaaggcacca ccacgctgcg caatatctat    1080
aactggcgtg ttaaagagac cgatcgcctg tttgcgatgg caacagaact gcgtaaagtc    1140 ggcgcgaag tggaagaggg gcacgattac attcgtatca ctcctccgga aaaactgaac    1200
tttgccgaga tcgcgacata caatgatcac cggatggcga tgtgtttctc gctggtggcg    1260
ttgtcagata caccagtgac gattcttgat cccaaatgca cggccaaaac atttccggat    1320
tatttcgagc agctggcgcg gattagccag gcagcctgaa tgaacaacgg gcaataaata    1380
gccaaatctt tctttatcaa aacgtcggca cattgtcggc gtttttttc ggacct         1436
```

```
<210> SEQ ID NO 11
<211> LENGTH: 1284
<212> TYPE: DNA
<213> ORGANISM: Escherichia coli
<220> FEATURE:
<221> NAME/KEY: CDS
<222> LOCATION: (1)...(1281)

<400> SEQUENCE: 11 atg gaa tcc ctg acg tta caa ccc atc gct cgt gtc gat ggc act att     48
Met Glu Ser Leu Thr Leu Gln Pro Ile Ala Arg Val Asp Gly Thr Ile
 1               5                  10                  15 aat ctg ccc ggt tcc aag agc gtt tct aac cgc gct tta ttg ctg gcg     96
Asn Leu Pro Gly Ser Lys Ser Val Ser Asn Arg Ala Leu Leu Leu Ala
             20                  25                  30 gca tta gca cac ggc aaa aca gta tta acc aat ctg ctg gat agc gat    144
Ala Leu Ala His Gly Lys Thr Val Leu Thr Asn Leu Leu Asp Ser Asp
         35                  40                  45 gac gtg cgc cat atg ctg aat gca tta aca gcg tta ggg gta agc tat    192
Asp Val Arg His Met Leu Asn Ala Leu Thr Ala Leu Gly Val Ser Tyr
     50                  55                  60 acg ctt tca gcc gat cgt acg cgt tgc gaa att atc ggt aac ggc ggt    240
Thr Leu Ser Ala Asp Arg Thr Arg Cys Glu Ile Ile Gly Asn Gly Gly
 65                  70                  75                  80 cca tta cac gca gaa ggt gcc ctg gag ttg ttc ctc ggt aac gcc gga    288
Pro Leu His Ala Glu Gly Ala Leu Glu Leu Phe Leu Gly Asn Ala Gly
                 85                  90                  95 acg gca atg cgt ccg ctg gcg gca gct ctt tgt ctg ggt agc aat gat    336
```

|  |  |  |  |  |  |  |  |  |  |  |  |  |  |
|---|---|---|---|---|---|---|---|---|---|---|---|---|---|
| Thr | Ala | Met | Arg | Pro | Leu | Ala | Ala | Ala | Leu | Cys | Leu | Gly | Ser | Asn | Asp |
|  |  |  | 100 |  |  |  | 105 |  |  |  | 110 |  |  |

```
att gtg ctg acc ggt gag ccg cgt atg aaa gaa cgc ccg att ggt cat      384
Ile Val Leu Thr Gly Glu Pro Arg Met Lys Glu Arg Pro Ile Gly His
        115                 120                 125 ctg gtg gat gcg ctg cgc ctg ggc ggg gcg aag atc act tac ctg gaa      432
Leu Val Asp Ala Leu Arg Leu Gly Gly Ala Lys Ile Thr Tyr Leu Glu
130                 135                 140 caa gaa aat tat ccg ccg ttg cgt tta cag ggc ggc ttt act ggc ggc      480
Gln Glu Asn Tyr Pro Pro Leu Arg Leu Gln Gly Gly Phe Thr Gly Gly
145                 150                 155                 160 aac gtt gac gtt gat ggc tcc gtt tcc agc caa ttc ctc acc gca ctg      528
Asn Val Asp Val Asp Gly Ser Val Ser Ser Gln Phe Leu Thr Ala Leu
                165                 170                 175 tta atg act gcg cct ctt gcg ccg gaa gat acg gtg att cgt att aaa      576
Leu Met Thr Ala Pro Leu Ala Pro Glu Asp Thr Val Ile Arg Ile Lys
            180                 185                 190 ggc gat ctg gtt tct aaa cct tat atc gac atc aca ctc aat ctg atg      624
Gly Asp Leu Val Ser Lys Pro Tyr Ile Asp Ile Thr Leu Asn Leu Met
        195                 200                 205 aag acg ttt ggt gtt gaa att gaa aat cag cac tat caa caa ttt gtc      672
Lys Thr Phe Gly Val Glu Ile Glu Asn Gln His Tyr Gln Gln Phe Val
210                 215                 220 gta aaa ggc ggg cag tct tat cag tct ccg ggt act tat ttg gtc gaa      720
Val Lys Gly Gly Gln Ser Tyr Gln Ser Pro Gly Thr Tyr Leu Val Glu
225                 230                 235                 240 ggc gat gca tct tcg gct tct tac ttt ctg gca gca gca gca atc aaa      768
Gly Asp Ala Ser Ser Ala Ser Tyr Phe Leu Ala Ala Ala Ala Ile Lys
                245                 250                 255 ggc ggc act gta aaa gtg acc ggt att gga cgt aac agt atg cag ggt      816
Gly Gly Thr Val Lys Val Thr Gly Ile Gly Arg Asn Ser Met Gln Gly
            260                 265                 270 gat att cgc ttt gct gat gtg ctg gaa aaa atg ggc gcg acc att tgc      864
Asp Ile Arg Phe Ala Asp Val Leu Glu Lys Met Gly Ala Thr Ile Cys
        275                 280                 285 tgg ggc gat gat tat att tcc tgc acg cgt ggt gaa ctg aac gct att      912
Trp Gly Asp Asp Tyr Ile Ser Cys Thr Arg Gly Glu Leu Asn Ala Ile
290                 295                 300 gat atg gat atg aac cat att cct gat gcg gcg atg acc att gcc acg      960
Asp Met Asp Met Asn His Ile Pro Asp Ala Ala Met Thr Ile Ala Thr
305                 310                 315                 320 gcg gcg tta ttt gca aaa ggc acc acc acg ctg cgc aat atc tat aac     1008
Ala Ala Leu Phe Ala Lys Gly Thr Thr Thr Leu Arg Asn Ile Tyr Asn
                325                 330                 335 tgg cgt gtt aaa gag acc gat cgc ctg ttt gcg atg gca aca gaa ctg     1056
Trp Arg Val Lys Glu Thr Asp Arg Leu Phe Ala Met Ala Thr Glu Leu
            340                 345                 350 cgt aaa gtc ggc gcg gaa gtg gaa gag ggg cac gat tac att cgt atc     1104
Arg Lys Val Gly Ala Glu Val Glu Glu Gly His Asp Tyr Ile Arg Ile
        355                 360                 365 act cct ccg gaa aaa ctg aac ttt gcc gag atc gcg aca tac aat gat     1152
Thr Pro Pro Glu Lys Leu Asn Phe Ala Glu Ile Ala Thr Tyr Asn Asp
370                 375                 380 cac cgg atg gcg atg tgt ttc tcg ctg gtg gcg ttg tca gat aca cca     1200
His Arg Met Ala Met Cys Phe Ser Leu Val Ala Leu Ser Asp Thr Pro
385                 390                 395                 400 gtg acg att ctt gat ccc aaa tgc acg gcc aaa aca ttt ccg gat tat     1248
Val Thr Ile Leu Asp Pro Lys Cys Thr Ala Lys Thr Phe Pro Asp Tyr
                405                 410                 415
```

```
ttc gag cag ctg gcg cgg att agc cag gca gcc tga                1284
Phe Glu Gln Leu Ala Arg Ile Ser Gln Ala Ala
            420                 425
```

<210> SEQ ID NO 12
<211> LENGTH: 427
<212> TYPE: PRT
<213> ORGANISM: Escherichia coli

<400> SEQUENCE: 12

```
Met Glu Ser Leu Thr Leu Gln Pro Ile Ala Arg Val Asp Gly Thr Ile
 1               5                  10                  15

Asn Leu Pro Gly Ser Lys Ser Val Ser Asn Arg Ala Leu Leu Leu Ala
                20                  25                  30

Ala Leu Ala His Gly Lys Thr Val Leu Thr Asn Leu Leu Asp Ser Asp
            35                  40                  45

Asp Val Arg His Met Leu Asn Ala Leu Thr Ala Leu Gly Val Ser Tyr
        50                  55                  60

Thr Leu Ser Ala Asp Arg Thr Arg Cys Glu Ile Ile Gly Asn Gly Gly
 65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125

Leu Val Asp Ala Leu Arg Leu Gly Gly Ala Lys Ile Thr Tyr Leu Glu
    130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
    290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
```

```
            355                 360                 365
Thr Pro Pro Glu Lys Leu Asn Phe Ala Glu Ile Ala Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
                420                 425

<210> SEQ ID NO 13
<211> LENGTH: 428
<212> TYPE: PRT
<213> ORGANISM: Clostridium acetobutylicum

<400> SEQUENCE: 13

Met Asn Cys Val Lys Ile Asn Pro Cys Cys Leu Lys Gly Asp Ile Lys
1               5                   10                  15

Ile Pro Pro Ser Lys Ser Leu Gly His Arg Ala Ile Ile Cys Ala Ala
                20                  25                  30

Leu Ser Glu Glu Ser Thr Ile Glu Asn Ile Ser Tyr Ser Lys Asp
        35                  40                  45

Ile Lys Ala Thr Cys Ile Gly Met Ser Lys Leu Gly Ala Leu Ile Ile
    50                  55                  60

Glu Asp Ala Lys Asp Asn Ser Thr Leu Lys Ile Lys Lys Gln Lys Leu
65                  70                  75                  80

Val Ser Lys Glu Lys Val Tyr Ile Asp Cys Ser Glu Ser Gly Ser Thr
                85                  90                  95

Val Arg Phe Leu Ile Pro Ile Ser Leu Ile Glu Glu Arg Asn Val Val
                100                 105                 110

Phe Asp Gly Gln Gly Lys Leu Ser Tyr Arg Pro Leu Asp Ser Tyr Phe
            115                 120                 125

Asn Ile Phe Asp Glu Lys Glu Ile Ala Tyr Ser His Pro Glu Gly Lys
    130                 135                 140

Val Leu Pro Leu Gln Ile Lys Gly Arg Leu Lys Ala Gly Met Phe Asn
145                 150                 155                 160

Leu Pro Gly Asn Ile Ser Ser Gln Phe Ile Ser Gly Leu Met Phe Ser
                165                 170                 175

Leu Pro Phe Leu Glu Gly Asp Ser Ile Ile Asn Ile Thr Thr Asn Leu
            180                 185                 190

Glu Ser Val Gly Tyr Val Asp Met Thr Ile Asp Met Leu Lys Lys Phe
        195                 200                 205

Gly Ile Glu Ile Glu Asn Lys Ala Tyr Lys Ser Phe Phe Ile Lys Gly
    210                 215                 220

Asn Gln Lys Cys Lys Gly Thr Lys Tyr Lys Val Glu Gly Asp Phe Ser
225                 230                 235                 240

Gln Ala Ala Phe Trp Leu Ser Ala Gly Ile Leu Asn Gly Asn Ile Asn
                245                 250                 255

Cys Lys Asp Leu Asn Ile Ser Ser Leu Gln Gly Asp Lys Val Ile Leu
            260                 265                 270

Asp Ile Leu Lys Lys Met Gly Gly Ala Ile Asp Glu Lys Ser Phe Ser
        275                 280                 285

Ser Lys Lys Ser His Thr His Gly Ile Val Ile Asp Ala Ser Gln Cys
    290                 295                 300
```

-continued

Pro Asp Leu Val Pro Ile Leu Ser Val Val Ala Ala Leu Ser Glu Gly
305                 310                 315                 320

Thr Thr Lys Ile Val Asn Ala Ala Arg Leu Arg Ile Lys Glu Ser Asp
                325                 330                 335

Arg Leu Lys Ala Met Ala Thr Glu Leu Asn Lys Leu Gly Ala Glu Val
            340                 345                 350

Val Glu Leu Glu Asp Gly Leu Leu Ile Glu Gly Lys Glu Lys Leu Lys
        355                 360                 365

Gly Gly Glu Val Glu Ser Trp Asn Asp His Arg Ile Ala Met Ala Leu
    370                 375                 380

Gly Ile Ala Ala Leu Arg Cys Glu Glu Ser Val Thr Ile Asn Gly Ser
385                 390                 395                 400

Glu Cys Val Ser Lys Ser Tyr Pro Gln Phe Trp Ser Asp Leu Lys Gln
                405                 410                 415

Leu Gly Gly Asp Val His Glu Trp Ser Leu Gly Glu
            420                 425

<210> SEQ ID NO 14
<211> LENGTH: 449
<212> TYPE: PRT
<213> ORGANISM: Pseudomonas sp. PG2982

<400> SEQUENCE: 14

Met Ser His Ser Ala Ser Pro Lys Pro Ala Thr Ala Arg Arg Ser Glu
1               5                   10                  15

Ala Leu Thr Gly Glu Ile Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Arg Ala Met Gln
    50                  55                  60

Ala Met Gly Ala Lys Ile Arg Lys Glu Gly Asp Val Trp Ile Ile Asn
65                  70                  75                  80

Gly Val Gly Asn Gly Cys Leu Leu Gln Pro Glu Ala Ala Leu Asp Phe
                85                  90                  95

Gly Asn Ala Gly Thr Gly Ala Arg Leu Thr Met Gly Leu Val Gly Thr
            100                 105                 110

Tyr Asp Met Lys Thr Ser Phe Ile Gly Asp Ala Ser Leu Ser Lys Arg
        115                 120                 125

Pro Met Gly Arg Val Leu Asn Pro Leu Arg Glu Met Gly Val Gln Val
    130                 135                 140

Glu Ala Ala Asp Gly Asp Arg Met Pro Leu Thr Leu Ile Gly Pro Lys
145                 150                 155                 160

Thr Ala Asn Pro Ile Thr Tyr Arg Val Pro Met Ala Ser Ala Gln Val
                165                 170                 175

Lys Ser Ala Val Leu Leu Ala Gly Leu Asn Thr Pro Gly Val Thr Thr
            180                 185                 190

Val Ile Glu Pro Val Met Thr Arg Asp His Thr Glu Lys Met Leu Gln
        195                 200                 205

Gly Phe Gly Ala Asp Leu Thr Val Glu Thr Asp Lys Asp Gly Val Arg
    210                 215                 220

His Ile Arg Ile Thr Gly Gln Gly Lys Leu Val Gly Gln Thr Ile Asp
225                 230                 235                 240

Val Pro Gly Asp Pro Ser Ser Thr Ala Phe Pro Leu Val Ala Ala Leu
                245                 250                 255

-continued

```
Leu Val Glu Gly Ser Asp Val Thr Ile Arg Asn Val Leu Met Asn Pro
            260                 265                 270

Thr Arg Thr Gly Leu Ile Leu Thr Leu Gln Glu Met Gly Ala Asp Ile
            275                 280                 285

Glu Val Leu Asn Ala Arg Leu Ala Gly Gly Glu Asp Val Ala Asp Leu
            290                 295                 300

Arg Val Arg Ala Ser Lys Leu Lys Gly Val Val Pro Pro Glu Arg
305                 310                 315                 320

Ala Pro Ser Met Ile Asp Glu Tyr Pro Val Leu Ala Ile Ala Ala Ser
                    325                 330                 335

Phe Ala Glu Gly Glu Thr Val Met Asp Gly Leu Asp Glu Leu Arg Val
            340                 345                 350

Lys Glu Ser Asp Arg Leu Ala Ala Val Ala Arg Gly Leu Glu Ala Asn
            355                 360                 365

Gly Val Asp Cys Thr Glu Gly Glu Met Ser Leu Thr Val Arg Gly Arg
            370                 375                 380

Pro Asp Gly Lys Gly Leu Gly Gly Thr Val Ala Thr His Leu Asp
385                 390                 395                 400

His Arg Ile Ala Met Ser Phe Leu Val Met Gly Leu Ala Ala Glu Lys
                    405                 410                 415

Pro Val Thr Val Asp Asp Ser Asn Met Ile Ala Thr Ser Phe Pro Glu
            420                 425                 430

Phe Met Asp Met Met Pro Gly Leu Gly Ala Lys Ile Glu Leu Ser Ile
            435                 440                 445

Leu
```

```
<210> SEQ ID NO 15
<211> LENGTH: 449
<212> TYPE: PRT
<213> ORGANISM: Achromobacter sp. LBAA

<400> SEQUENCE: 15

Met Ser His Ser Ala Ser Pro Lys Pro Ala Thr Ala Arg Arg Ser Glu
  1               5                  10                  15

Ala Leu Thr Gly Glu Ile Arg Ile Pro Gly Asp Lys Ser Ile Ser His
             20                  25                  30

Arg Ser Phe Met Phe Gly Gly Leu Ala Ser Gly Glu Thr Arg Ile Thr
         35                  40                  45

Gly Leu Leu Glu Gly Glu Asp Val Ile Asn Thr Gly Arg Ala Met Gln
     50                  55                  60

Ala Met Gly Ala Lys Ile Arg Lys Glu Gly Asp Val Trp Ile Ile Asn
 65                  70                  75                  80

Gly Val Gly Asn Gly Cys Leu Leu Gln Pro Glu Ala Ala Leu Asp Phe
                 85                  90                  95

Gly Asn Ala Gly Thr Gly Ala Arg Leu Thr Met Gly Leu Val Gly Thr
            100                 105                 110

Tyr Asp Met Lys Thr Ser Phe Ile Gly Asp Ala Ser Leu Ser Lys Arg
        115                 120                 125

Pro Met Gly Arg Val Leu Asn Pro Leu Arg Glu Met Gly Val Gln Val
    130                 135                 140

Glu Ala Ala Asp Gly Asp Arg Met Pro Leu Thr Leu Ile Gly Pro Lys
145                 150                 155                 160

Thr Ala Asn Pro Ile Thr Tyr Arg Val Pro Met Ala Ser Ala Gln Val
                165                 170                 175
```

-continued

```
Lys Ser Ala Val Leu Leu Ala Gly Leu Asn Thr Pro Gly Val Thr Thr
            180                 185                 190

Val Ile Glu Pro Val Met Thr Arg Asp His Thr Glu Lys Met Leu Gln
        195                 200                 205

Gly Phe Gly Ala Asp Leu Thr Val Glu Thr Asp Lys Asp Gly Val Arg
    210                 215                 220

His Ile Arg Ile Thr Gly Gln Gly Lys Leu Val Gly Gln Thr Ile Asp
225                 230                 235                 240

Val Pro Gly Asp Pro Ser Ser Thr Ala Phe Pro Leu Val Ala Ala Leu
                245                 250                 255

Leu Val Glu Gly Ser Asp Val Thr Ile Arg Asn Val Leu Met Asn Pro
            260                 265                 270

Thr Arg Thr Gly Leu Ile Leu Thr Leu Gln Glu Met Gly Ala Asp Ile
        275                 280                 285

Glu Val Leu Asn Ala Arg Leu Ala Gly Gly Glu Asp Val Ala Asp Leu
    290                 295                 300

Arg Val Arg Ala Ser Lys Leu Lys Gly Val Val Val Pro Pro Glu Arg
305                 310                 315                 320

Ala Pro Ser Met Ile Asp Glu Tyr Pro Val Leu Ala Ile Ala Ala Ser
                325                 330                 335

Phe Ala Glu Gly Glu Thr Val Met Asp Gly Leu Asp Glu Leu Arg Val
            340                 345                 350

Lys Glu Ser Asp Arg Leu Ala Ala Val Ala Arg Gly Leu Glu Ala Asn
        355                 360                 365

Gly Val Asp Cys Thr Glu Gly Glu Met Ser Leu Thr Val Arg Gly Arg
    370                 375                 380

Pro Asp Gly Lys Gly Leu Gly Gly Gly Thr Val Ala Thr His Leu Asp
385                 390                 395                 400

His Arg Ile Ala Met Ser Phe Leu Val Met Gly Leu Ala Ala Glu Lys
                405                 410                 415

Pro Val Thr Val Asp Asp Ser Asn Met Ile Ala Thr Ser Phe Pro Glu
            420                 425                 430

Phe Met Asp Met Met Pro Gly Leu Gly Ala Lys Ile Glu Leu Ser Ile
        435                 440                 445

Leu
```

<210> SEQ ID NO 16
<211> LENGTH: 455
<212> TYPE: PRT
<213> ORGANISM: Agrobacterium sp. CP4

<400> SEQUENCE: 16

```
Met Ser His Gly Ala Ser Ser Arg Pro Ala Thr Ala Arg Lys Ser Ser
  1               5                  10                  15

Gly Leu Ser Gly Thr Val Arg Ile Pro Gly Asp Lys Ser Ile Ser His
                 20                  25                  30

Arg Ser Phe Met Phe Gly Gly Leu Ala Ser Gly Glu Thr Arg Ile Thr
             35                  40                  45

Gly Leu Leu Glu Gly Glu Asp Val Ile Asn Thr Gly Lys Ala Met Gln
         50                  55                  60

Ala Met Gly Ala Arg Ile Arg Lys Glu Gly Asp Thr Trp Ile Ile Asp
 65                  70                  75                  80

Gly Val Gly Asn Gly Gly Leu Leu Ala Pro Glu Ala Pro Leu Asp Phe
                 85                  90                  95
```

```
Gly Asn Ala Ala Thr Gly Cys Arg Leu Thr Met Gly Leu Val Gly Val
            100                 105                 110
Tyr Asp Phe Asp Ser Thr Phe Ile Gly Asp Ala Ser Leu Thr Lys Arg
        115                 120                 125
Pro Met Gly Arg Val Leu Asn Pro Leu Arg Glu Met Gly Val Gln Val
    130                 135                 140
Lys Ser Glu Asp Gly Asp Arg Leu Pro Val Thr Leu Arg Gly Pro Lys
145                 150                 155                 160
Thr Pro Thr Pro Ile Thr Tyr Arg Val Pro Met Ala Ser Ala Gln Val
                165                 170                 175
Lys Ser Ala Val Leu Leu Ala Gly Leu Asn Thr Pro Gly Ile Thr Thr
            180                 185                 190
Val Ile Glu Pro Ile Met Thr Arg Asp His Thr Glu Lys Met Leu Gln
        195                 200                 205
Gly Phe Gly Ala Asn Leu Thr Val Glu Thr Asp Ala Asp Gly Val Arg
    210                 215                 220
Thr Ile Arg Leu Glu Gly Arg Gly Lys Leu Thr Gly Gln Val Ile Asp
225                 230                 235                 240
Val Pro Gly Asp Pro Ser Ser Thr Ala Phe Pro Leu Val Ala Ala Leu
                245                 250                 255
Leu Val Pro Gly Ser Asp Val Thr Ile Leu Asn Val Leu Met Asn Pro
            260                 265                 270
Thr Arg Thr Gly Leu Ile Leu Thr Leu Gln Glu Met Gly Ala Asp Ile
        275                 280                 285
Glu Val Ile Asn Pro Arg Leu Ala Gly Gly Glu Asp Val Ala Asp Leu
    290                 295                 300
Arg Val Arg Ser Ser Thr Leu Lys Gly Val Thr Val Pro Glu Asp Arg
305                 310                 315                 320
Ala Pro Ser Met Ile Asp Glu Tyr Pro Ile Leu Ala Val Ala Ala Ala
                325                 330                 335
Phe Ala Glu Gly Ala Thr Val Met Asn Gly Leu Glu Glu Leu Arg Val
            340                 345                 350
Lys Glu Ser Asp Arg Leu Ser Ala Val Ala Asn Gly Leu Lys Leu Asn
        355                 360                 365
Gly Val Asp Cys Asp Glu Gly Glu Thr Ser Leu Val Val Arg Gly Arg
    370                 375                 380
Pro Asp Gly Lys Gly Leu Gly Asn Ala Ser Gly Ala Ala Val Ala Thr
385                 390                 395                 400
His Leu Asp His Arg Ile Ala Met Ser Phe Leu Val Met Gly Leu Val
                405                 410                 415
Ser Glu Asn Pro Val Thr Val Asp Asp Ala Thr Met Ile Ala Thr Ser
            420                 425                 430
Phe Pro Glu Phe Met Asp Leu Met Ala Gly Leu Gly Ala Lys Ile Glu
        435                 440                 445
Leu Ser Asp Thr Lys Ala Ala
    450                 455

<210> SEQ ID NO 17
<211> LENGTH: 428
<212> TYPE: PRT
<213> ORGANISM: Bacillus subtilis

<400> SEQUENCE: 17

Met Lys Arg Asp Lys Val Gln Thr Leu His Gly Glu Ile His Ile Pro
```

-continued

```
                1               5                      10                       15
         Gly Asp Lys Ser Ile Ser His Arg Ser Val Met Phe Gly Ala Leu Ala
                         20                      25                      30

Ala Gly Thr Thr Thr Val Lys Asn Phe Leu Pro Gly Ala Asp Cys Leu
                         35                      40                      45

Ser Thr Ile Asp Cys Phe Arg Lys Met Gly Val His Ile Glu Gln Ser
                         50                      55                      60

Ser Ser Asp Val Val Ile His Gly Lys Gly Ile Asp Ala Leu Lys Glu
         65                      70                      75                      80

Pro Glu Ser Leu Leu Asp Val Gly Asn Ser Gly Thr Thr Ile Arg Leu
                         85                      90                      95

Met Leu Gly Ile Leu Ala Gly Arg Pro Phe Tyr Ser Ala Val Ala Gly
                         100                     105                     110

Asp Glu Ser Ile Ala Lys Arg Pro Met Lys Arg Val Thr Glu Pro Leu
                         115                     120                     125

Lys Lys Met Gly Ala Lys Ile Asp Gly Arg Ala Gly Gly Glu Phe Thr
                         130                     135                     140

Pro Leu Ser Val Ser Gly Ala Ser Leu Lys Gly Ile Asp Tyr Val Ser
         145                     150                     155                     160

Pro Val Ala Ser Ala Gln Ile Lys Ser Ala Val Leu Leu Ala Gly Leu
                         165                     170                     175

Gln Ala Glu Gly Thr Thr Val Thr Glu Pro His Lys Ser Arg Asp
                         180                     185                     190

His Thr Glu Arg Met Leu Ser Ala Phe Gly Val Lys Leu Ser Glu Asp
                         195                     200                     205

Gln Thr Ser Val Ser Ile Ala Gly Gly Gln Lys Leu Thr Ala Ala Asp
                         210                     215                     220

Ile Phe Val Pro Gly Asp Ile Ser Ser Ala Ala Phe Phe Leu Ala Ala
         225                     230                     235                     240

Gly Ala Met Val Pro Asn Ser Arg Ile Val Leu Lys Asn Val Gly Leu
                         245                     250                     255

Asn Pro Thr Arg Thr Gly Ile Ile Asp Val Leu Gln Asn Met Gly Ala
                         260                     265                     270

Lys Leu Glu Ile Lys Pro Ser Ala Asp Ser Gly Ala Glu Pro Tyr Gly
                         275                     280                     285

Asp Leu Ile Ile Glu Thr Ser Ser Leu Lys Ala Val Glu Ile Gly Gly
                         290                     295                     300

Asp Ile Ile Pro Arg Leu Ile Asp Glu Ile Pro Ile Ile Ala Leu Leu
         305                     310                     315                     320

Ala Thr Gln Ala Glu Gly Thr Thr Val Ile Lys Asp Ala Ala Glu Leu
                         325                     330                     335

Lys Val Lys Glu Thr Asn Arg Ile Asp Thr Val Val Ser Glu Leu Arg
                         340                     345                     350

Lys Leu Gly Ala Glu Ile Glu Pro Thr Ala Asp Gly Met Lys Val Tyr
                         355                     360                     365

Gly Lys Gln Thr Leu Lys Gly Gly Ala Val Ser Ser His Gly Asp
                         370                     375                     380

His Arg Ile Gly Met Met Leu Gly Ile Ala Ser Cys Ile Thr Glu Glu
         385                     390                     395                     400

Pro Ile Glu Ile Glu His Thr Asp Ala Ile His Val Ser Tyr Pro Thr
                         405                     410                     415

Phe Phe Glu His Leu Asn Lys Leu Ser Lys Lys Ser
                         420                     425
```

<210> SEQ ID NO 18
<211> LENGTH: 432
<212> TYPE: PRT
<213> ORGANISM: Staphylococcus aureus

<400> SEQUENCE: 18

```
Met Val Ser Glu Gln Ile Ile Asp Ile Ser Gly Pro Leu Lys Gly Glu
 1               5                  10                  15

Ile Glu Val Pro Gly Asp Lys Ser Met Thr His Arg Ala Ile Met Leu
            20                  25                  30

Ala Ser Leu Ala Glu Gly Thr Ser Asn Ile Tyr Lys Pro Leu Leu Gly
        35                  40                  45

Glu Asp Cys Arg Arg Thr Met Asp Ile Phe Arg Leu Leu Gly Val Asp
    50                  55                  60

Ile Lys Glu Asp Glu Asp Lys Leu Val Val Asn Ser Pro Gly Tyr Lys
65                  70                  75                  80

Ala Phe Lys Thr Pro His Gln Val Leu Tyr Thr Gly Asn Ser Gly Thr
                85                  90                  95

Thr Thr Arg Leu Leu Ala Gly Leu Leu Ser Gly Leu Gly Ile Glu Ser
            100                 105                 110

Val Leu Ser Gly Asp Val Ser Ile Gly Lys Arg Pro Met Asp Arg Val
        115                 120                 125

Leu Arg Pro Leu Lys Leu Met Asp Ala Asn Ile Glu Gly Ile Glu Asp
    130                 135                 140

Asn Tyr Thr Pro Leu Ile Ile Lys Pro Ser Val Ile Lys Gly Ile Asn
145                 150                 155                 160

Tyr Gln Met Glu Val Ala Ser Ala Gln Val Lys Ser Ala Ile Leu Phe
                165                 170                 175

Ala Ser Leu Phe Ser Asn Asp Thr Thr Val Ile Lys Glu Leu Asp Val
            180                 185                 190

Ser Arg Asn His Thr Glu Thr Met Phe Arg His Phe Asn Ile Pro Ile
        195                 200                 205

Glu Ala Glu Arg Leu Ser Ile Thr Thr Thr Pro Asp Ala Ile Gln His
    210                 215                 220

Ile Lys Pro Ala Asp Phe His Val Pro Gly Asp Ile Ser Ser Ala Ala
225                 230                 235                 240

Phe Phe Ile Val Ala Ala Leu Ile Thr Pro Glu Ser Asp Val Thr Ile
                245                 250                 255

His Asn Val Gly Ile Asn Pro Thr Arg Ser Gly Ile Ile Asp Ile Val
            260                 265                 270

Glu Lys Met Gly Gly Asn Ile Gln Leu Phe Asn Gln Thr Thr Gly Ala
        275                 280                 285

Glu Pro Thr Ala Ser Ile Arg Ile Gln Tyr Thr Pro Met Leu Gln Pro
    290                 295                 300

Ile Thr Ile Glu Gly Glu Leu Val Pro Lys Ala Ile Asp Glu Leu Pro
305                 310                 315                 320

Val Ile Ala Leu Leu Cys Thr Gln Ala Val Gly Thr Ser Thr Ile Lys
                325                 330                 335

Asp Ala Glu Glu Leu Lys Val Lys Glu Thr Asn Arg Ile Asp Thr Thr
            340                 345                 350

Ala Asp Met Leu Asn Leu Leu Gly Phe Glu Leu Gln Pro Thr Asn Asp
        355                 360                 365

Gly Leu Ile Ile His Pro Ser Glu Phe Lys Thr Asn Ala Thr Val Asp
```

-continued

```
                370                 375                 380
Ser Leu Thr Asp His Arg Ile Gly Met Met Leu Ala Val Ala Ser Leu
385                 390                 395                 400

Leu Ser Ser Glu Pro Val Lys Ile Lys Gln Phe Asp Ala Val Asn Val
                405                 410                 415

Ser Phe Pro Gly Phe Leu Pro Lys Leu Lys Leu Leu Glu Asn Glu Gly
                420                 425                 430

<210> SEQ ID NO 19
<211> LENGTH: 443
<212> TYPE: PRT
<213> ORGANISM: Dichelobacter nodosus

<400> SEQUENCE: 19

Met Met Thr Asn Ile Trp His Thr Ala Pro Val Ser Ala Leu Ser Gly
  1               5                  10                  15

Glu Ile Thr Ile Cys Gly Asp Lys Ser Met Ser His Arg Ala Leu Leu
                 20                  25                  30

Leu Ala Ala Leu Ala Glu Gly Gln Thr Glu Ile Arg Gly Phe Leu Ala
             35                  40                  45

Cys Ala Asp Cys Leu Ala Thr Arg Gln Ala Leu Arg Ala Leu Gly Val
         50                  55                  60

Asp Ile Gln Arg Glu Lys Glu Ile Val Thr Ile Arg Gly Val Gly Phe
65                  70                  75                  80

Leu Gly Leu Gln Pro Pro Lys Ala Pro Leu Asn Met Gln Asn Ser Gly
                 85                  90                  95

Thr Ser Met Arg Leu Leu Ala Gly Ile Leu Ala Ala Gln Arg Phe Glu
                100                 105                 110

Ser Val Leu Cys Gly Asp Glu Ser Leu Glu Lys Arg Pro Met Gln Arg
            115                 120                 125

Ile Ile Thr Pro Leu Val Gln Met Gly Ala Lys Ile Val Ser His Ser
        130                 135                 140

Asn Phe Thr Ala Pro Leu His Ile Ser Gly Arg Pro Leu Thr Gly Ile
145                 150                 155                 160

Asp Tyr Ala Leu Pro Leu Pro Ser Ala Gln Leu Lys Ser Cys Leu Ile
                165                 170                 175

Leu Ala Gly Leu Leu Ala Asp Gly Thr Thr Arg Leu His Thr Cys Gly
            180                 185                 190

Ile Ser Arg Asp His Thr Glu Arg Met Leu Pro Leu Phe Gly Gly Ala
        195                 200                 205

Leu Glu Ile Lys Lys Glu Gln Ile Ile Val Thr Gly Gly Gln Lys Leu
    210                 215                 220

His Gly Cys Val Leu Asp Ile Val Gly Asp Leu Ser Ala Ala Ala Phe
225                 230                 235                 240

Phe Met Val Ala Ala Leu Ile Ala Pro Arg Ala Glu Val Val Ile Arg
                245                 250                 255

Asn Val Gly Ile Asn Pro Thr Arg Ala Ala Ile Ile Thr Leu Leu Gln
            260                 265                 270

Lys Met Gly Gly Arg Ile Glu Leu His His Gln Arg Phe Trp Gly Ala
        275                 280                 285

Glu Pro Val Ala Asp Ile Val Val Tyr His Ser Lys Leu Arg Gly Ile
    290                 295                 300

Thr Val Ala Pro Glu Trp Ile Ala Asn Ala Ile Asp Glu Leu Pro Ile
305                 310                 315                 320
```

```
Phe Phe Ile Ala Ala Ala Cys Ala Glu Gly Thr Thr Phe Val Gly Asn
            325                 330                 335

Leu Ser Glu Leu Arg Val Lys Glu Ser Asp Arg Leu Ala Ala Met Ala
        340                 345                 350

Gln Asn Leu Gln Thr Leu Gly Val Ala Cys Asp Val Gly Ala Asp Phe
        355                 360                 365

Ile His Ile Tyr Gly Arg Ser Asp Arg Gln Phe Leu Pro Ala Arg Val
    370                 375                 380

Asn Ser Phe Gly Asp His Arg Ile Ala Met Ser Leu Ala Val Ala Gly
385                 390                 395                 400

Val Arg Ala Ala Gly Glu Leu Leu Ile Asp Asp Gly Ala Val Ala Ala
                405                 410                 415

Val Ser Met Pro Gln Phe Arg Asp Phe Ala Ala Ile Gly Met Asn
            420                 425                 430

Val Gly Glu Lys Asp Ala Lys Asn Cys His Asp
        435                 440

<210> SEQ ID NO 20
<211> LENGTH: 427
<212> TYPE: PRT
<213> ORGANISM: Aeromonas salmonicida

<400> SEQUENCE: 20

Met Asn Ser Leu Arg Leu Glu Pro Ile Ser Arg Val Ala Gly Glu Val
1               5                   10                  15

Asn Leu Pro Gly Ser Lys Ser Val Ser Asn Gly Ala Leu Leu Leu Ala
            20                  25                  30

Ala Leu Ala Arg Gly Thr Thr Arg Leu Thr Asn Leu Leu Asp Ser Asp
        35                  40                  45

Asp Ile Arg His Met Leu Ala Ala Leu Thr Gln Leu Gly Val Lys Tyr
    50                  55                  60

Lys Leu Ser Ala Asp Lys Thr Glu Cys Thr Val His Gly Leu Gly Arg
65                  70                  75                  80

Ser Phe Ala Val Ser Ala Pro Val Asn Leu Phe Leu Gly Asn Ala Gly
                85                  90                  95

Thr Ala Met Arg Pro Leu Cys Ala Ala Leu Cys Leu Gly Ser Gly Glu
            100                 105                 110

Tyr Met Leu Gly Gly Glu Pro Arg Met Glu Glu Arg Pro Ile Gly His
        115                 120                 125

Leu Val Asp Cys Leu Ala Leu Lys Gly Ala His Ile Gln Tyr Leu Lys
    130                 135                 140

Lys Asp Gly Tyr Pro Pro Leu Val Val Asp Ala Lys Gly Leu Trp Gly
145                 150                 155                 160

Gly Asp Val His Val Asp Gly Ser Val Ser Ser Gln Phe Leu Thr Ala
                165                 170                 175

Phe Leu Met Ala Ala Pro Ala Met Ala Pro Val Ile Pro Arg Ile His
            180                 185                 190

Ile Lys Gly Glu Leu Val Ser Lys Pro Tyr Ile Asp Ile Thr Leu His
        195                 200                 205

Ile Met Asn Ser Ser Gly Val Val Ile Glu His Asp Asn Tyr Lys Leu
    210                 215                 220

Phe Tyr Ile Lys Gly Asn Gln Ser Ile Val Ser Pro Gly Asp Phe Leu
225                 230                 235                 240

Val Glu Gly Asp Ala Ser Ser Ala Ser Tyr Phe Leu Ala Ala Gly Ala
                245                 250                 255
```

```
Ile Lys Gly Lys Val Arg Val Thr Gly Ile Gly Lys His Ser Ile Gly
            260                 265                 270

Asp Ile His Phe Ala Asp Val Leu Glu Arg Met Gly Ala Arg Ile Thr
            275                 280                 285

Trp Gly Asp Asp Phe Ile Glu Ala Glu Gln Gly Pro Leu His Gly Val
            290                 295                 300

Asp Met Asp Met Asn His Ile Pro Asp Val Gly His Asp His Ser Gly
305                 310                 315                 320

Gln Ser His Cys Leu Pro Arg Val Pro Pro His Ser Gln His Leu Gln
                325                 330                 335

Leu Ala Val Arg Asp Asp Arg Cys Thr Pro Cys Thr His Gly His Arg
            340                 345                 350

Arg Ala Gln Ala Gly Val Ser Glu Gly Thr Thr Phe Ile Thr Arg
            355                 360                 365

Asp Ala Ala Asp Pro Ala Gln Ala Arg Arg Asp Arg His Leu Gln Ala
            370                 375                 380

Ser Arg Ile Ala Met Cys Phe Ser Leu Val Ala Leu Ser Asp Ile Ala
385                 390                 395                 400

Val Thr Ile Asn Asp Pro Gly Cys Thr Ser Lys Thr Phe Pro Asp Tyr
                405                 410                 415

Phe Asp Lys Leu Ala Ser Val Ser Gln Ala Val
            420                 425

<210> SEQ ID NO 21
<211> LENGTH: 444
<212> TYPE: PRT
<213> ORGANISM: Arabidopsis thaliana

<400> SEQUENCE: 21

Lys Ala Ser Glu Ile Val Leu Gln Pro Ile Arg Glu Ile Ser Gly Leu
1               5                   10                  15

Ile Lys Leu Pro Gly Ser Lys Ser Leu Ser Asn Arg Ile Leu Leu Leu
            20                  25                  30

Ala Ala Leu Ser Glu Gly Thr Thr Val Val Asp Asn Leu Leu Asn Ser
        35                  40                  45

Asp Asp Ile Asn Tyr Met Leu Asp Ala Leu Lys Arg Leu Gly Leu Asn
    50                  55                  60

Val Glu Thr Asp Ser Glu Asn Asn Arg Ala Val Val Glu Gly Cys Gly
65                  70                  75                  80

Gly Ile Phe Pro Ala Ser Ile Asp Ser Lys Ser Asp Ile Glu Leu Tyr
                85                  90                  95

Leu Gly Asn Ala Gly Thr Ala Met Arg Pro Leu Thr Ala Ala Val Thr
            100                 105                 110

Ala Ala Gly Gly Asn Ala Ser Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Glu Cys Thr Leu Gly Thr Asn Cys Pro Pro Val Arg Val
145                 150                 155                 160

Asn Ala Asn Gly Gly Leu Pro Gly Gly Lys Val Lys Leu Ser Gly Ser
                165                 170                 175

Ile Ser Ser Gln Tyr Leu Thr Ala Leu Leu Met Ser Ala Pro Leu Ala
            180                 185                 190

Leu Gly Asp Val Glu Ile Glu Ile Val Asp Lys Leu Ile Ser Val Pro
```

```
                195                 200                 205
Tyr Val Glu Met Thr Leu Lys Leu Met Glu Arg Phe Gly Val Ser Val
    210                 215                 220

Glu His Ser Asp Ser Trp Asp Arg Phe Phe Val Lys Gly Gly Gln Lys
225                 230                 235                 240

Tyr Lys Ser Pro Gly Asn Ala Tyr Val Glu Gly Asp Ala Ser Ser Ala
                245                 250                 255

Cys Tyr Phe Leu Ala Gly Ala Ala Ile Thr Gly Glu Thr Val Thr Val
            260                 265                 270

Glu Gly Cys Gly Thr Thr Ser Leu Gln Gly Asp Val Lys Phe Ala Glu
        275                 280                 285

Val Leu Glu Lys Met Gly Cys Lys Val Ser Trp Thr Glu Asn Ser Val
    290                 295                 300

Thr Val Thr Gly Pro Pro Arg Asp Ala Phe Gly Met Arg His Leu Arg
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Thr Ile Arg Asp Val
            340                 345                 350

Ala Ser Trp Arg Val Lys Glu Thr Glu Arg Met Ile Ala Ile Cys Thr
        355                 360                 365

Glu Leu Arg Lys Leu Gly Ala Thr Val Glu Glu Gly Ser Asp Tyr Cys
    370                 375                 380

Val Ile Thr Pro Pro Lys Lys Val Lys Thr Ala Glu Ile Asp Thr Tyr
385                 390                 395                 400

Asp Asp His Arg Met Ala Met Ala Phe Ser Leu Ala Ala Cys Ala Asp
                405                 410                 415

Val Pro Ile Thr Ile Asn Asp Ser Gly Cys Thr Arg Lys Thr Phe Pro
            420                 425                 430

Asp Tyr Phe Gln Val Leu Glu Arg Ile Thr Lys His
        435                 440

<210> SEQ ID NO 22
<211> LENGTH: 444
<212> TYPE: PRT
<213> ORGANISM: Nicotiana tabacum

<400> SEQUENCE: 22

Lys Pro Asn Glu Ile Val Leu Gln Pro Ile Lys Asp Ile Ser Gly Thr
1               5                   10                  15

Val Lys Leu Pro Gly Ser Lys Ser Leu Ser Asn Arg Ile Leu Leu Leu
            20                  25                  30

Ala Ala Leu Ser Lys Gly Arg Thr Val Val Asp Asn Leu Leu Ser Ser
        35                  40                  45

Asp Asp Ile His Tyr Met Leu Gly Ala Leu Lys Thr Leu Gly Leu His
    50                  55                  60

Val Glu Asp Asp Asn Glu Asn Gln Arg Ala Ile Val Glu Gly Cys Gly
65                  70                  75                  80

Gly Gln Phe Pro Val Gly Lys Lys Ser Glu Glu Ile Gln Leu Phe
                85                  90                  95

Leu Gly Asn Ala Gly Thr Ala Met Arg Pro Leu Thr Ala Ala Val Thr
            100                 105                 110

Val Ala Gly Gly His Ser Arg Tyr Val Leu Asp Gly Val Pro Arg Met
        115                 120                 125
```

-continued

```
Arg Glu Arg Pro Ile Gly Asp Leu Val Asp Gly Leu Lys Gln Leu Gly
130                 135                 140

Ala Glu Val Asp Cys Phe Leu Gly Thr Asn Cys Pro Pro Val Arg Ile
145                 150                 155                 160

Val Ser Lys Gly Gly Leu Pro Gly Gly Lys Val Lys Leu Ser Gly Ser
                165                 170                 175

Ile Ser Ser Gln Tyr Leu Thr Ala Leu Leu Met Ala Ala Pro Leu Ala
                180                 185                 190

Leu Gly Asp Val Glu Ile Glu Ile Asp Lys Leu Ile Ser Val Pro
            195                 200                 205

Tyr Val Glu Met Thr Leu Lys Leu Met Glu Arg Phe Gly Val Ser Val
    210                 215                 220

Glu His Thr Ser Ser Trp Asp Lys Phe Leu Val Arg Gly Gly Gln Lys
225                 230                 235                 240

Tyr Lys Ser Pro Gly Lys Ala Tyr Val Glu Gly Asp Ala Ser Ser Ala
                245                 250                 255

Ser Tyr Phe Leu Ala Gly Ala Ala Val Thr Gly Gly Thr Val Thr Val
                260                 265                 270

Glu Gly Cys Gly Thr Ser Ser Leu Gln Gly Asp Val Lys Phe Ala Glu
            275                 280                 285

Val Leu Glu Lys Met Gly Ala Glu Val Thr Trp Thr Glu Asn Ser Val
    290                 295                 300

Thr Val Lys Gly Pro Pro Arg Asn Ser Ser Gly Met Lys His Leu Arg
305                 310                 315                 320

Ala Val Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Ile Ala Ile Cys Thr
    355                 360                 365

Glu Leu Arg Lys Leu Gly Ala Thr Val Val Glu Gly Ser Asp Tyr Cys
370                 375                 380

Ile Ile Thr Pro Pro Glu Lys Leu Asn Val Thr Glu Ile Asp Thr Tyr
385                 390                 395                 400

Asp Asp His Arg Met Ala Met Ala Phe Ser Leu Ala Ala Cys Ala Asp
                405                 410                 415

Val Pro Val Thr Ile Lys Asp Pro Gly Cys Thr Arg Lys Thr Phe Pro
            420                 425                 430

Asn Tyr Phe Asp Val Leu Gln Gln Tyr Ser Lys His
    435                 440
```

<210> SEQ ID NO 23
<211> LENGTH: 444
<212> TYPE: PRT
<213> ORGANISM: Petunia x hybrida

<400> SEQUENCE: 23

```
Lys Pro Ser Glu Ile Val Leu Gln Pro Ile Lys Glu Ile Ser Gly Thr
1               5                   10                  15

Val Lys Leu Pro Gly Ser Lys Ser Leu Ser Asn Arg Ile Leu Leu Leu
            20                  25                  30

Ala Ala Leu Ser Glu Gly Thr Thr Val Val Asp Asn Leu Leu Ser Ser
        35                  40                  45

Asp Asp Ile His Tyr Met Leu Gly Ala Leu Lys Thr Leu Gly Leu His
    50                  55                  60
```

```
Val Glu Glu Asp Ser Ala Asn Gln Arg Ala Val Val Glu Gly Cys Gly
 65                  70                  75                  80

Gly Leu Phe Pro Val Gly Lys Glu Ser Lys Glu Glu Ile Gln Leu Phe
                 85                  90                  95

Leu Gly Asn Ala Gly Thr Ala Met Arg Pro Leu Thr Ala Ala Val Thr
            100                 105                 110

Val Ala Gly Gly Asn Ser Arg Tyr Val Leu Asp Gly Val Pro Arg Met
        115                 120                 125

Arg Glu Arg Pro Ile Ser Asp Leu Val Asp Gly Leu Lys Gln Leu Gly
    130                 135                 140

Ala Glu Val Asp Cys Phe Leu Gly Thr Lys Cys Pro Pro Val Arg Ile
145                 150                 155                 160

Val Ser Lys Gly Gly Leu Pro Gly Gly Lys Val Lys Leu Ser Gly Ser
                165                 170                 175

Ile Ser Ser Gln Tyr Leu Thr Ala Leu Leu Met Ala Ala Pro Leu Ala
            180                 185                 190

Leu Gly Asp Val Glu Ile Glu Ile Ile Asp Lys Leu Ile Ser Val Pro
        195                 200                 205

Tyr Val Glu Met Thr Leu Lys Leu Met Glu Arg Phe Gly Ile Ser Val
210                 215                 220

Glu His Ser Ser Ser Trp Asp Arg Phe Val Arg Gly Gly Gln Lys
225                 230                 235                 240

Tyr Lys Ser Pro Gly Lys Ala Phe Val Glu Gly Asp Ala Ser Ser Ala
                245                 250                 255

Ser Tyr Phe Leu Ala Gly Ala Ala Val Thr Gly Gly Thr Ile Thr Val
            260                 265                 270

Glu Gly Cys Gly Thr Asn Ser Leu Gln Gly Asp Val Lys Phe Ala Glu
        275                 280                 285

Val Leu Glu Lys Met Gly Ala Glu Val Thr Trp Thr Glu Asn Ser Val
    290                 295                 300

Thr Val Lys Gly Pro Pro Arg Ser Ser Gly Arg Lys His Leu Arg
305                 310                 315                 320

Ala Ile Asp Val Asn Met Asn Lys Met Pro Asp Val Ala Met Thr Leu
                325                 330                 335

Ala Val Val Ala Leu Tyr Ala Asp Gly Pro Thr Ala Ile Arg Asp Val
            340                 345                 350

Ala Ser Trp Arg Val Lys Glu Thr Glu Arg Met Ile Ala Ile Cys Thr
        355                 360                 365

Glu Leu Arg Lys Leu Gly Ala Thr Val Glu Glu Gly Pro Asp Tyr Cys
    370                 375                 380

Ile Ile Thr Pro Pro Glu Lys Leu Asn Val Thr Asp Ile Asp Thr Tyr
385                 390                 395                 400

Asp Asp His Arg Met Ala Met Ala Phe Ser Leu Ala Ala Cys Ala Asp
                405                 410                 415

Val Pro Val Thr Ile Asn Asp Pro Gly Cys Thr Arg Lys Thr Phe Pro
            420                 425                 430

Asn Tyr Phe Asp Val Leu Gln Gln Tyr Ser Lys His
        435                 440

<210> SEQ ID NO 24
<211> LENGTH: 444
<212> TYPE: PRT
<213> ORGANISM: Zea mays
```

<400> SEQUENCE: 24

```
Ala Gly Ala Glu Glu Ile Val Leu Gln Pro Ile Lys Glu Ile Ser Gly
  1               5                  10                  15
Thr Val Lys Leu Pro Gly Ser Lys Ser Leu Ser Asn Arg Ile Leu Leu
             20                  25                  30
Leu Ala Ala Leu Ser Glu Gly Thr Thr Val Val Asp Asn Leu Leu Asn
         35                  40                  45
Ser Glu Asp Val His Tyr Met Leu Gly Ala Leu Arg Thr Leu Gly Leu
     50                  55                  60
Ser Val Glu Ala Asp Lys Ala Ala Lys Arg Ala Val Val Gly Cys
 65                  70                  75                  80
Gly Gly Lys Phe Pro Val Glu Asp Ala Lys Glu Glu Val Gln Leu Phe
                 85                  90                  95
Leu Gly Asn Ala Gly Thr Ala Met Arg Pro Leu Thr Ala Ala Val Thr
            100                 105                 110
Ala Ala Gly Gly Asn Ala Thr Tyr Val Leu Asp Gly Val Pro Arg Met
        115                 120                 125
Arg Glu Arg Pro Ile Gly Asp Leu Val Val Gly Leu Lys Gln Leu Gly
    130                 135                 140
Ala Asp Val Asp Cys Phe Leu Gly Thr Asp Cys Pro Pro Val Arg Val
145                 150                 155                 160
Asn Gly Ile Gly Gly Leu Pro Gly Gly Lys Val Lys Leu Ser Gly Ser
                165                 170                 175
Ile Ser Ser Gln Tyr Leu Ser Ala Leu Leu Met Ala Ala Pro Leu Ala
            180                 185                 190
Leu Gly Asp Val Glu Ile Glu Ile Ile Asp Lys Leu Ile Ser Ile Pro
        195                 200                 205
Tyr Val Glu Met Thr Leu Arg Leu Met Glu Arg Phe Gly Val Lys Ala
    210                 215                 220
Glu His Ser Asp Ser Trp Asp Arg Phe Tyr Ile Lys Gly Gly Gln Lys
225                 230                 235                 240
Tyr Lys Ser Pro Lys Asn Ala Tyr Val Glu Gly Asp Ala Ser Ser Ala
                245                 250                 255
Ser Tyr Phe Leu Ala Gly Ala Ala Ile Thr Gly Gly Thr Val Thr Val
            260                 265                 270
Glu Gly Cys Gly Thr Thr Ser Leu Gln Gly Asp Val Lys Phe Ala Glu
        275                 280                 285
Val Leu Glu Met Met Gly Ala Lys Val Thr Trp Thr Glu Thr Ser Val
    290                 295                 300
Thr Val Thr Gly Pro Pro Arg Glu Pro Phe Gly Arg Lys His Leu Lys
305                 310                 315                 320
Ala Ile Asp Val Asn Met Asn Lys Met Pro Asp Val Ala Met Thr Leu
                325                 330                 335
Ala Val Val Ala Leu Phe Ala Asp Gly Pro Thr Ala Ile Arg Asp Val
            340                 345                 350
Ala Ser Trp Arg Val Lys Glu Thr Glu Arg Met Val Ala Ile Arg Thr
        355                 360                 365
Glu Leu Thr Lys Leu Gly Ala Ser Val Glu Glu Gly Pro Asp Tyr Cys
    370                 375                 380
Ile Ile Thr Pro Pro Glu Lys Leu Asn Val Thr Ala Ile Asp Thr Tyr
385                 390                 395                 400
Asp Asp His Arg Met Ala Met Ala Phe Ser Leu Ala Ala Cys Ala Glu
                405                 410                 415
```

```
Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440
```

<210> SEQ ID NO 25
<211> LENGTH: 442
<212> TYPE: PRT
<213> ORGANISM: Bordetella pertussis

<400> SEQUENCE: 25

```
Met Ser Gly Leu Ala Tyr Leu Asp Leu Pro Ala Ala Arg Leu Ala Arg
  1               5                  10                  15

Gly Glu Val Ala Leu Pro Gly Ser Lys Ser Ile Ser Asn Arg Val Leu
             20                  25                  30

Leu Leu Ala Ala Leu Ala Glu Gly Ser Thr Glu Ile Thr Gly Leu Leu
         35                  40                  45

Asp Ser Asp Thr Arg Val Met Leu Ala Ala Leu Arg Gln Leu Gly
     50                  55                  60

Val Ser Val Gly Glu Val Ala Asp Gly Cys Val Thr Ile Glu Gly Val
 65                  70                  75                  80

Ala Arg Phe Pro Thr Glu Gln Ala Glu Leu Phe Leu Gly Asn Ala Gly
                 85                  90                  95

Thr Ala Phe Arg Pro Leu Thr Ala Ala Leu Ala Leu Met Gly Gly Asp
                100                 105                 110

Tyr Arg Leu Ser Gly Val Pro Arg Met His Glu Arg Pro Ile Gly Asp
            115                 120                 125

Leu Val Asp Ala Leu Arg Gln Phe Gly Ala Gly Ile Glu Tyr Leu Gly
    130                 135                 140

Gln Ala Gly Tyr Pro Pro Leu Arg Ile Gly Gly Ser Ile Arg Val
145                 150                 155                 160

Asp Gly Pro Val Arg Val Glu Gly Ser Val Ser Gln Phe Leu Thr
                165                 170                 175

Ala Leu Leu Met Ala Ala Pro Val Leu Ala Arg Arg Ser Gly Gln Asp
                180                 185                 190

Ile Thr Ile Glu Val Val Gly Glu Leu Ile Ser Lys Pro Tyr Ile Glu
            195                 200                 205

Ile Thr Leu Asn Leu Met Ala Arg Phe Gly Val Ser Val Arg Arg Asp
    210                 215                 220

Gly Trp Arg Ala Phe Thr Ile Ala Arg Asp Ala Val Tyr Arg Gly Pro
225                 230                 235                 240

Gly Arg Met Ala Ile Glu Gly Asp Ala Ser Thr Ala Ser Tyr Phe Leu
                245                 250                 255

Ala Leu Gly Ala Ile Gly Gly Pro Val Arg Val Thr Gly Val Gly
                260                 265                 270

Glu Asp Ser Ile Gln Gly Asp Val Ala Phe Ala Ala Thr Leu Ala Ala
            275                 280                 285

Met Gly Ala Asp Val Arg Tyr Gly Pro Gly Trp Ile Glu Thr Arg Gly
    290                 295                 300

Val Arg Val Ala Glu Gly Gly Arg Leu Lys Ala Phe Asp Ala Asp Phe
305                 310                 315                 320

Asn Leu Ile Pro Asp Ala Ala Met Thr Ala Thr Leu Ala Leu Tyr
                325                 330                 335

Ala Asp Gly Pro Cys Arg Leu Arg Asn Ile Gly Ser Trp Arg Val Lys
```

```
                      340                 345                 350
Glu Thr Asp Arg Ile His Ala Met His Thr Glu Leu Glu Lys Leu Gly
        355                 360                 365

Ala Gly Val Gln Ser Gly Ala Asp Trp Leu Glu Val Ala Pro Pro Glu
        370                 375                 380

Pro Gly Gly Trp Arg Asp Ala His Ile Gly Thr Trp Asp Asp His Arg
385                 390                 395                 400

Met Ala Met Cys Phe Leu Leu Ala Ala Phe Gly Pro Ala Ala Val Arg
                405                 410                 415

Ile Leu Asp Pro Gly Cys Val Ser Lys Thr Phe Pro Asp Tyr Phe Asp
                420                 425                 430

Val Tyr Ala Gly Leu Leu Ala Ala Arg Asp
        435                 440
```